the route of administration and the relative potency of the compounds.

The invention is illustrated by the following Preparations and Examples. Temperatures are given in degrees Centigrade.

PREPARATION 1

(a) A mixture of 4-cyanopyridine (31.2 g), ammonium persulphate (136.8 g), methanol (450 ml), concentrated sulphuric acid (16.2 ml), and water (210 ml) was heated under reflux for 24 hours, and the methanol was removed by distillation. Crushed ice (450 g) was added and the mixture was adjusted to pH 12 with 10 M sodium hydroxide and extracted with chloroform. The chloroform extracts were combined and evaporated and the residue was purified by elution from a silica gel column with methanol-chloroform (7.5% v/v) to give 4-cyano-2-hydroxymethylpyridine (18.5 g, 46%) m.p. 92°–94°.

(b) A solution of 4-cyano-2-hydroxymethylpyridine (0.5 g) in tetrahydrofuran (25 ml) was added dropwise over 20 minutes to a stirred mixture of lithium aluminium hydride (0.25 g) in tetrahydrofuran (30 ml) and the mixture was stirred at room temperature for 2 hours. Wet tetrahydrofuran followed by 0.35 ml of 16% w/w aqueous sodium hydroxide and water were added and the mixture was filtered. The filtrate was evaporated to give crude 4-aminomethyl-2-hydroxymethylpyridine (0.28 g).

NMR (CDCl$_3$): p.p.m., assignment, multiplicity, integral; 3.87, CH$_2$NH$_2$, s, 1.7; 4.61, CH$_2$OH, s, 2; 7.11, 5-pyridyl proton, d of d, 1; 7.30, 3-pyridyl proton, d, 1; 8.4, 6-pyridyl proton, d, 1.

(c) A solution of 4-aminomethyl-2-hydroxymethylpyridine (1.38 g) in aqueous formaldehyde (25% w/w, 12 ml) was hydrogenated at 344 kPa and 30° for 23 hours with 10% palladium on charcoal catalyst. The mixture was filtered and the filtrate was extracted with chloroform. The chloroform phase was extracted with water at pH 5 and this aqueous extract was adjusted to pH 12 and extracted with chloroform. This chloroform extract was evaporated to give 4-dimethylaminomethyl-2-hydroxymethylpyridine (0.47 g) as an oil.

NMR (CDCl$_3$): p.p.m., assignment, multiplicity, integral; 2.26, N(CH$_3$)$_2$, s, 5.5; 3.42, CH$_2$N(CH$_3$)$_2$, s, 2; 3.75, OH, broad, 1.3; 4.78, CH$_2$OH, s, 2; 7.19+7.28, 5+3 pyridyl protons, d of d+d, 2.1; 8.49, 6-pyridyl proton, d, 1.

PREPARATION 2

Ammonium persulphate (102.7 g) in water (200 ml) was added over 40 minutes to a refluxing solution of 4-dimethylaminomethylpyridine (40.86 g), methanol (450 ml), water (210 ml) and concentrated sulphuric acid (30 ml). The resulting solution was refluxed for 2 hours, water (300 ml) was added and the methanol was distilled off. The cooled solution was basified and extracted with chloroform to give 4-dimethylaminomethyl-2-hydroxymethylpyridine (19.65 g) b.p. 92°–120°/0.06 mm Hg.

PREPARATION 3

4-Dimethylaminomethyl-2-hydroxymethylpyridine (13.45 g) in dichloromethane (200 ml) was added dropwise to a stirred solution of thionyl chloride (30 ml) in dichloromethane (150 ml). The resulting red mixture was stirred for 1 hour then concentrated in vacuo. The residue was treated with ether (300 ml) to yield a crystalline solid. Recrystallisation from methanol/ether (1:3) yielded 2-chloromethyl-4-dimethylaminomethylpyridine hydrochloride (20.04 g) as an orange solid m.p. 202°–204°.

PREPARATION 4

Cysteamine hydrochloride (3.75 g) was added to a stirred solution of sodium ethoxide (prepared from 2.83 g sodium) in ethanol (200 ml) and the mixture was cooled to less than 10°. 2-Chloromethyl-4-dimethylaminomethylpyridine dihydrochloride (7.3 g) was added portionwise and the solution was stirred for 1 hour. Water (200 ml) was added, the pH was adjusted to ca. 4 with hydrochloric acid and the volume was reduced to ca. 100 ml. The solution was extracted with chloroform, the aqueous phase was basified to pH 12 and extracted with chloroform to give 2-(4-dimethylaminomethyl-2-pyridylmethylthio)ethylamine (4.7 g) as an oil.

NMR(CDCl$_3$) p.p.m., assignment, multiplicity, integral: 1.51, NH$_2$, s, 2.2; 2.28, N(CH$_3$)$_2$, s, 6; 2.65+2.85, SCH$_2$CH$_2$NH$_2$, mx2, 4.2; 3.46, CH$_2$SCH$_2$CH$_2$NH$_2$, s, 2.1; 3.86, CH$_2$N(CH$_3$)$_2$, s, 2.1; 7.17, 5-pyridyl proton, d of d, 1; 7.36, 3-pyridyl proton, d, 1.1; 8.49, 6-pyridyl proton, d, 1.1.

PREPARATION 5

(a) Ammonium persulphate (54.8 g) in water (150 ml) and 4-cyanobutyric acid (68 g) in water (300 ml) were added separately and simultaneously over 30 minutes to a mixture of 4-dimethylaminomethylpyridine (16.32 g), silver nitrate (4 g), water (200 ml) and concentrated sulphuric acid (25 ml) stirred at 80°. The reaction mixture was stirred at 80° for 1.5 hours, cooled, poured onto crushed ice (400 g) and aqueous ammonia (28% w/w, 200 ml). The solution was extracted with chloroform (900 ml) and the chloroform extracts were washed with dilute sodium hydroxide, dried over magnesium sulphate, and concentrated in vacuo to give 2-(3-cyanopropyl)-4-dimethylaminomethylpyridine (9 g) as a clear oil b.p. 110°–112°/0.1 mm Hg.

NMR (CDCl$_3$): p.p.m., assignment, multiplicity, integral; 2.15+2.23+2.40, CH$_2$CH$_2$CH$_2$CN+N(CH$_3$)$_2$+CH$_2$CH$_2$CH$_2$CN, m+s+m, 10; 2.92, CH CH$_2$CH$_2$CN, t, 2; 3.41, CH$_2$N(CH$_3$)$_2$, s, 2; 7.1, 5+3 pyridyl protons, m, 2; 8.46, 6-pyridyl proton, d, 1.

(b) 2-(3-Cyanopropyl)-4-dimethylaminomethylpyridine (1 g) in diethyl ether (15 ml) was added dropwise to a rapidly stirred suspension of lithium aluminium hydride (0.76 g) in ether (45 ml). The solution was stirred for 2.5 hours. Wet tetrahydrofuran, followed by 16% sodium hydroxide (1 ml) and then water was added and the mixture was filtered. The filtrate was evaporated to give 4-(4-dimethylaminomethyl-2-pyridyl)butylamine (1.02 g) as a clear oil.

NMR (CDCl$_3$): p.p.m., assignment, multiplicity, integral; 1.64+1.70, NH$_2$+CH$_2$(CH$_2$)$_2$CH$_2$NH$_2$, s+m, 6.3; 2.23, N(CH$_3$)$_2$, s, 6; ca 2.75, CH$_2$(CH$_2$)$_2$CH$_2$NH$_2$, m, 3.9; 3.39, CH$_2$N(CH$_3$)$_2$, s, 2; 7.1, 5+3 pyridyl protons, m, 2; 8.46, 6-pyridyl proton, d, 1.

EXAMPLE 1

A solution of 2-(4-dimethylaminomethyl-2-pyridylmethylthio)ethylamine (0.5 g) and 2-nitroamino-5-(6-methyl-3-pyridylmethyl)-4-pyrimidone (0.7 g) in pyridine (3 ml) was heated under reflux for 3.5 hours and evaporated to dryness. The residue was purified by

PROCESS FOR PREPARING TRIARYLMETHANE DERIVATIVES

This is a division of application Ser. No. 699,584 filed June 24, 1976 now U.S. Pat. No. 4,045,458.

BACKGROUND OF THE INVENTION

This invention relates to a process for preparing colourless chromogenic compounds which form coloured markings upon contact with acidic materials by electron donor-acceptor colour-forming reaction.

Particularly, this invention relates to a novel process for preparing triarylmethane derivatives represented by the following general formulae (I), (II), (III) and (IV):

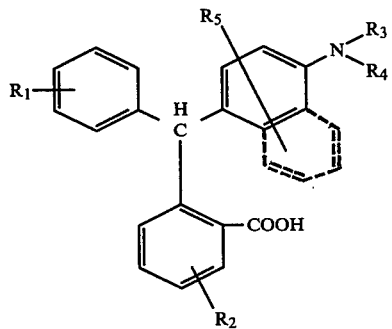

(I)

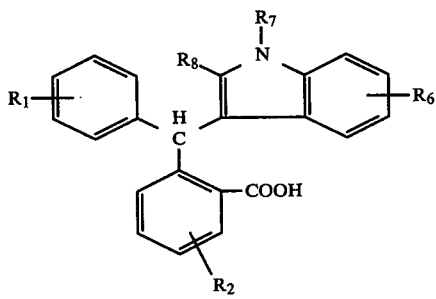

(II)

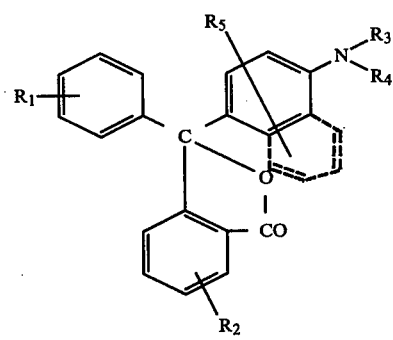

(III)

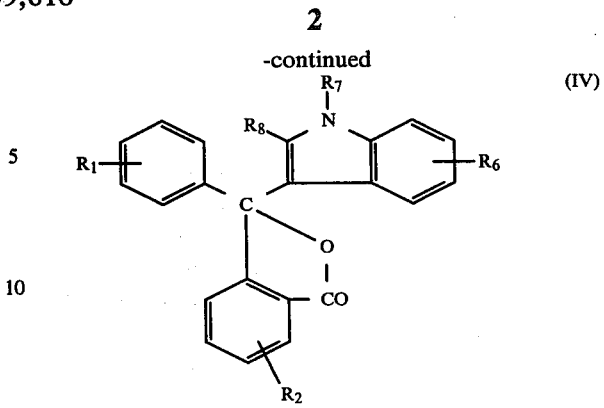

wherein each of $R_1$ and $R_2$ is at least one of hydrogen, halogen, nitro group, alkyl group, substituted alkyl group, amino group, substituted amino group, hydroxyl group, substituted hydroxyl group, thiohydroxyl group, or substituted thiohydroxyl group; each of $R_3$ and $R_4$ is hydrogen, substituted or unsubstituted alkyl group, cycloalkyl group, substituted or unsubstituted aralkyl group, substituted or unsubstituted aryl group, or substituted or unsubstituted unsaturated alkyl group, or one or both of $R_3$ and $R_4$ together with the adjacent nitrogen atom may form a heterocyclic ring; $R_5$ is at least one of hydrogen, halogen, alkyl group, nitro group, substituted or unsubstituted amino group, substituted or unsubstituted hydroxyl group, substituted or unsubstituted thiohydroxyl group; $R_6$ is at least one of hydrogen, halogen, lower alkyl group, lower alkoxyl group, amino group, lower alkylamino group, nitro group, phenyl group or phenoxy group; $R_7$ is hydrogen, alkyl group, aralkyl group or phenyl group; and $R_8$ is lower alkyl group or substituted or unsubstituted phenyl group.

There are known several methods for preparing triarylmethane derivatives represented by the general formula (I), for example, U.S. Pat. No. Re. 23,024 discloses a method in which the triarylmethane derivative is prepared from m-dimethylamino-benzoic acid and Michler's hydrol by condensation reaction. Another method for preparing triarylmethane derivative by condensation reaction of dimethylaniline with o-phthalaldehydric acid is described in "Beilsteins Handbuch der Organische Chemie", Vol. 14, page 549. However, these methods give triarylmethane derivative in low yields because a large amount of by-products is produced. Furthermore, these methods give only limited compound having a symmetrical structure.

The triarylmethane derivatives having the general formula (II) are novel compounds which are synthesized for the first time by this invention.

The known method for preparing triarylmethane derivatives represented by the general formula (III) and (IV) is disclosed in U.S. Pat. Nos. 2,443,092 and 2,597,965, "Beilsteins Handbuch der Organische Chemie", vol. 18, page 617 and Moriga & Oda, "Kogyo Kagaku Zasshi", vol. 64, page 1226, (1961), in which triarylmethane derivatives are prepared from dimethylaniline and phthalic anhydride by condensation. Another method is described in U.S. Pat. Nos. 3,491,112 and 3,491,116 and in "Beilsteins Handbuch der Organische Chemie", vol 18, pages 618–619, in which benzophenone-2-carboxylic acid is first prepared from dimethylaniline and phthalic anhydride and then triarylmethane derivative is prepared from the resultant ben- -continued

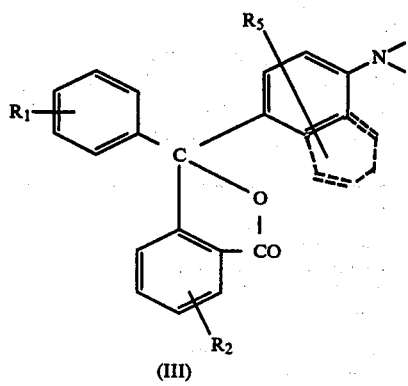

(III)

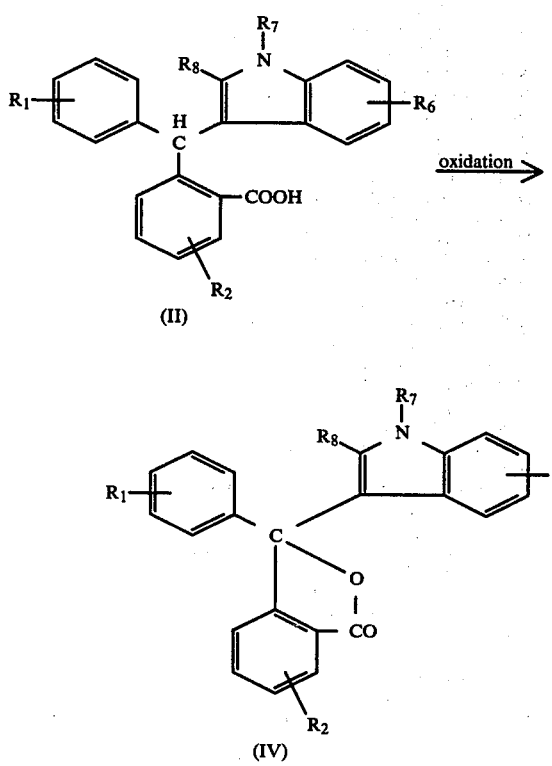

wherein $R_1$, $R_2$, $R_3$, $R_4$, $R_5$, $R_6$, $R_7$ and $R_8$ are the same as described above.

DETAILED DESCRIPTION OF THE INVENTION 3-phenylphthalide derivative represented by the above described general formula (V) which is used in this invention is prepared, as shown as follows, from benzene derivative (VIII) and o-phthalaldehydic acid derivative (IX) by dehydration condensation, or from benzaldehyde derivative (X) and benzoic acid derivative (XI) by dehydration condensation:

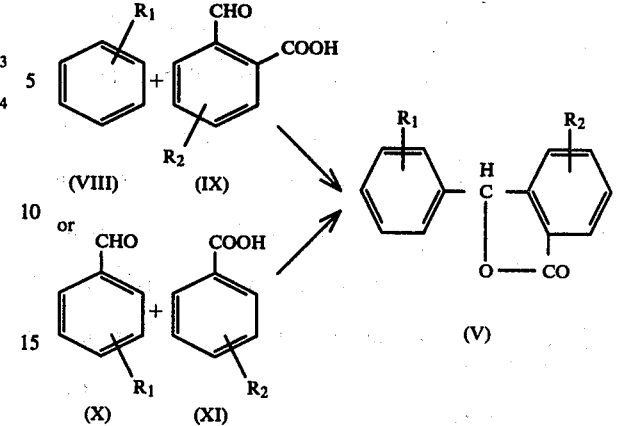

wherein $R_1$ and $R_2$ are the same as described above.

As the typical compounds of 3-phenylphthalide derivatives represented by the above general formula (V) which are used in this invention, the following compounds may be exemplified;

3-(4'-dimethylaminophenyl)phthalide,
3-(4'-dimethylamino-2'-methylphenyl)phthalide,
3-(4'-dimethylamino-2'-methoxyphenyl)phthalide,
3-(4'-dimethylamino-2'-methylthiophenyl)phthalide,
3-(4'-dimethylamino-2'-chlorophenyl)phthalide,
3-(4'-dimethylamino-2'-diethylaminophenyl)phthalide,
3-(4'-diethylaminophenyl)phthalide,
3-(4'-diethylamino-2'-chlorophenyl)phthalide,
3-(4'-diethylamino-2'-methoxyphenyl)phthalide,
3-[4'-(N-ethyl-N-benzyl)aminophenyl]phthalide,
3-[4'-(N-methyl-N-P-tolyl)aminophenyl]phthalide,
3-(4'-pyrrolidinophenyl)phthalide,
4-(julolidine-6'-yl)phthalide,
3-phenyl-6-dimethylaminophthalide,
3-phenyl-6-diethylaminophthalide,
3-[2'(or 3', or 4')-methylphenyl]-6-dimethylaminophthalide,
3-[2'(or 3', or 4')-methoxyphenyl]-6-dimethylaminophthalide,
3-[2'(or 3', or 4')-methoxyphenyl]-6-diethylaminophthalide,
3-[2'-(or 3', or 4')-chlorophenyl]-6-dimethylaminophthalide,
3-[2'-(or 3', or 4')-nitrophenyl]-6-dimethylaminophthalide,
3-[2'-(or 3', or 4')-nitrophenyl]-6-diethylaminophthalide,
3-[2', 3'(or 2', 4')-dimethylphenyl]-6-dimethylaminophthalide,
3-[2', 3'(or 2', 4')-dimethoxyphenyl]-6-dimethylaminophthalide,
3-[2', 3'(or 2',4')-dimethoxyphenyl]-6-diethylaminophthalide,
3-[2',3'(or 2', 4')-dichlorophenyl]-6-dimethylaminophthalide,
3-(2'-methyl-4'-methoxyphenyl)-6-dimethylaminophthalide,
3-(2'-methoxy-4'-methylphenyl)-6-dimethylaminophthalide,
3-[2'(or 3', or 4')-dimethylaminophenyl]-6-dimethylaminophthalide,
3-[2'(or 3', or 4')-dimethylaminophenyl]-6-diethylaminophthalide, 3-[2'(or 3', or 4')-dimethylaminophenyl]-6-N-methyl-N-P-tolylaminophthalide,
3-[2'(or 3', or 4')-dimethylaminophenyl]-6-N-ethyl-N-benzylaminophthalide,
3-[(2'(or 3', or 4')-diethylaminophenyl]-6-dimethylaminophthalide,
3-[2'(or 3', or 4')-diethylaminophenyl]-6-diethylaminophthalide,
3-[2'(or 3', or 4')-dimethylaminophenyl]-5-chloro-6-dimethylaminophthalide,
3-[2'(or 3', or 4')-dimethylaminophenyl]-5-chloro-6-diethylaminophthalide,
3-[2'(or 3', or 4')-dimethylaminophenyl]-6-diallylaminophthalide,
3-[2'(or 3', or 4')-dimethylaminophenyl]-6-dipropargylamino-phthalide,
3-[2'(or 3', or 4')-dimethylaminophenyl]-6-pyrrolidinophthalide,
3-[2'(or 3', or 4')-dimethylaminophenyl]-6-pyrimidinophthalide,
3-[2'(or 3', or 4')-dimethylaminophenyl]-6-morpholinophthalide,
3-(4'-pyrrolidinophenyl)-6-dimethylaminophthalide,
3-(4'-pyrimidinophenyl)-6-dimethylaminophthalide,
3-(julolidine-6'-yl)-6-dimethylaminophthalide,
3-(4'-morpholinophenyl)-6-dimethylaminophthalide,
3-[4'-(N-methyl-N-benzyl)aminophenyl]-6-dimethylaminophthalide,
3-[4'-(N-methyl-N-benzyl)aminophenyl]-6-diethylaminophthalide,
3-[4'-(N-ethyl-N-benzyl)aminophenyl]-6-dimethylaminophthalide,
3-[4'-(N-methyl-N-para-tolyl)aminophenyl]-6-dimethylamino-phthalide,
3-[4'-(N-ethyl-N-para-tolyl)aminophenyl]-6-dimethylaminophthalide,
3-[4'-(N-ethyl-N-para-tolyl)aminophenyl]-6-diethylaminophthalide,
3-(4'-diallylaminophenyl)-6-dimethylaminophthalide,
3-(4'-dipropargylaminophenyl)-6-dimethylaminophthalide,
3-(4'-dimethylamino-2'-methylphenyl)-6-dimethylaminophthalide,
3-(4'-diethylamino-2'-methylphenyl)-6-dimethylaminophthalide,
3-(4'-dimethylamino-2'-chlorophenyl)-6-dimethylaminophthalide,
3-(4'-diethylamino-2'-chlorophenyl)-6-dimethylaminophthalide,
3-(4'-dimethylamino-2'-methoxyphenyl)-6-dimethylaminophthalide,
3-(4'-diethylamino-2'-methoxyphenyl)-6-dimethylaminophthalide,
3-(4'-dimethylamino-2'-methylthiophenyl)-6-dimethylaminopnthalide,
3-(4'-diethylamino-2'-methylphenyl)-5-chloro-6-dimethylaminophthalide,
3-(4'-dietylamino-2'-methylphenyl)-5-chloro-6-diethylaminophthalide,
3-(4'-diethylamino-2'-methoxyphenyl)-5-chloro-6-dimethylaminophthalide,
3-(4'-diethylamino-2'-methoxyphenyl)-5-chloro-6-diethylaminophthalide,
3-(4'-dimethylaminophenyl)-6-methoxyphthalide,
3-(4'-diethylaminophenyl)-6-ethoxyphthalide,
3-(4'-diethylaminophenyl)-6-methoxyphthalide and
3-(4'-diethylamino-2'-methoxyphenyl)-6-methoxyphthalide.

Among the above mentioned 3-phenylphthalide derivatives, those having $R_2$ at the 6 position are preferably used and preferably $R_2$ is an substituted amino group.

Among the typical compounds of aniline derivatives represented by the above described general formula (VI) which are used in this invention there may be included the following compounds:

aniline, N—methylaniline,
N—ethylaniline, o-toluidine,
m-toluidine, m-nitroaniline,
m-phenylenediamine, m-chloroaniline,
m-bromoaniline, o-anisidine,
o-phenetidine, 2.5-dichloroaniline,
N,N—dimethylaniline, N,N—diethylaniline,
N—(2-ethylhexyl)-N—methylaniline,
N,N—dibutylaniline, N—dodecyl-N—ethylaniline,
N,N—diethyl-m-toluidine, N,N—diethyl-o-toluidine,
N,N—dibenzylaniline, N—methyl-N—benzylaniline,
N—ethyl-N—benzylaniline, diphenylamine,
N—benzyldiphenylamine, 4-benzyloxydiphenylamine,
N—ethyl-4-ethoxydiphenylamine,
N—methyldiphenylamine, N—ethyldiphenylamine,
N,N—diethyl-o-anisidine, N,N—dimethyl-o-phenetidine,
N,N—diethyl-m-acetoxyaniline,
N,N—dimethyl-m-nitroaniline,
N,N—diethyl-m-nitroaniline,
N,N—dimethyl-o-chloroaniline,
N,N—dimethyl-m-chloroaniline,
N,N—diethyl-m-chloroaniline,
N,N—dimethyl-o-bromoaniline,
N,N—dimethyl-m-bromoaniline,
N,N—diethyl-o-bromoaniline,
N,N—diethyl-m-bromoaniline,
N,N—diethyl-m-hydroxyaniline,
N,N—bis(β-cyanoethyl)aniline,
N,N—bis(β-chloroethyl)aniline,
N,N—bis(β-bromoethyl)aniline,
N,N—bis(β-ethoxyethyl)aniline,
N,N—bis(βL-cyanoethyl)-m-toluidine,
N,N—bis(β-chloroethyl)-m-toluidine,
N,N—bis(β-bromoethyl)-m-toluisine,
N—ethyl-N—(β-chloroethyl)-m-toluidine,
N,N—bis(β-ethoxyethyl)-m-toluisine,
N—ethyl-N—phenethylaniline,
N—ethoxycarbonylmethyl-N—cyclohexylaniline,
N,N—diethyl-m-phenylenediamine,
N,N—diethyl-o-phenylenediamine,
N,N,N',N',—tetraethyl-m-phenylenediamine,
N,N,N',N',—tetraethyl-o-phenylenediamine,
N—cyclohexyl-N—methylaniline,
N—phenylmorpholine, N—phenylpiperidine,
N—phenylpyrrolidine, N—phenylimidazoline,
N—phenylpyrazolidine, N—phenylpiperazine,
jalolidine, 1-naphthylamine,
N—methyl-1-naphthylamine, N— ethyl-1-naphthylamine,
N—phenyl-1-naphthylamine,
N,N—dimethyl-1-naphthylamine,
N,N—diethyl-1-naphthylamine,
5-chloro-N,N—dimethyl-1-naphthylamine,
5-bromo-N,N—dimethyl-1-naphthylamine,
5-ethoxy-N,N—diethyl-1-naphthylamine,
5-benzyloxy-N,N—dimethyl-1-naphthylamine,
N—ethyl-N—benzyl-1-naphthylamine,
N,N—bis(β-chloroethyl)-1-naphthylamine,
N,N—bis(β-bromoethyl)-1-naphthylamine,
N,N—bis(β-cyanoethyl)-1-naphthylamine,
N,N—bis(β-methoxyethyl)-1-naphthylamine,
N,N—bis(β-ethoxyethyl)-1-naphthylamine and
N—phenyl-N—methyl-1-naphthylamine.

Among the typical compounds of indole derivatives represented by the above mentioned general formula (VII) which are used in this invention there may be included the following compounds:

2-methylindole, 2-ethylindole,
2-phenylindole, 2-(2'-methylphenyl)indole,

-continued 2-methyl-5-chloroindole, 2-methyl-5-ethoxyindole,
2-methyl-7-phenylindole, 2-methyl-5-aminoindole,
1,2-dimethylindole, 1-methyl-2-phenylindole,
1.2.5-trimethylindole, 1.2-dimethyl-5-methoxyindole,
1.2-dimethyl-5-phenoxyindole,
1.2-dimethyl-5-nitroindole,
1-methyl-2-(4'-chlorophenyl)indole,
1-methyl-2-(4'-ethoxyphenyl)indole,
1-methyl-2-(4'-ethoxyphenyl)-5-dimethylaminoindole,
1-benzyl-2-methylindole, 1-benzyl-2.5-dime thylindole
1-benzyl-2-methyl-5-methoxyindole,
1.2-dimethyl-7-phenylindole,
1-phenyl-2.5-dimethylindole,
1-phenyl-2.5-diethylindole and
1.2-dimethyl-5.6-dichloroindole.

In the practice of the invention, 3-phenylphthalide derivative is made to react with aniline derivative or indole derivative in the presence of Friedel-Crafts type catalyst, if necessary, with use of a suitable solvent, at the temperature of 0° to 180° C. for the period between several minutes and several decades of hours.

As a Friedel-Crafts type catalyst, acidic halide Lewis acid catalysts such as $AlCl_3$, $AlBr_3$, $BeCl_2$, $CdCl_2$, $ZnCl_2$, $BF_3$, $BCl_3$, $GaCl_3$, $GaBr_3$, $TiCl_4$, $TiBr_4$, $ZnCl_4$, $SnCl_4$, $SnBr_4$, $SbCl_5$, $SbCl_3$, $BiCl_3$, $FeCl_3$, $UCl_4$, $PF_5$, $SbF_5$, $AsF_5$ and mixed pentafluorides of Nb and Ta; metal alkyl Lewis acid catalysts such as $Al_2Cl_3(CH_3)_3+HCl$, $AlCl_2(C_2H_5)$, $AlCl(C_2H_5)_2$, $AlBr_3(C_2H_5)_3$, $Al(C_2H_5)_2Br$, $Al(C_2H_5)Br_2$, $Al(C_2H_5)_3$, $Al(t-C_4H_9)_3$, $Al(i-C_4H_9)_3$, $AuBr_2C_2H_5$, $Be(C_2H_5)_2$, $BRx_3$, $MgRx_2$, $Rx_2Mg.MgX_2$, $TiCl_3CH_3$, $TiCl_3(C_2H_5)$ and $Zn(C_2H_5)_2$, wherein Rx is alkyl group and X is halogen; metal alkoxide Lewis acid catalysts such as $Al(OC_6H_5)_3$, aluminum alkoxides, $AlCl_2ORx$, $AlCl_3.Ti(ORx)_4$, $Ti(BuO)_4$ and $Ti(i-PrO)_4$, wherein Rx is alkyl group; Brønsted acid catalysts such as, phosphoric acid, polyphosphoric acid, perchloric acid, chlorosulfonic acid, fluosulfonic acid, alkane sulfonic acids such as ethane sulfonic acid, p-toluenesulfonic acid, acetic acid, chloroacetic acids, trifluoroacetic acid, sulfuric acid, hydrogen halides and alkyl halides; acidic oxide and sulfide (acidic chalcide) catalysts such as alumina, $Al_2O_3.CaO$, $Al_2O_3.Cr_2O_3$, $Al_2O_3.Fe_2O_3$, $Al_2O_3.V_2O_3$, alumino-silicates (natural), bauxite, bentonite clay, BeO, acid activated clay, chromia (with silica-alumina), $Cr_2O_3$(synthetic), $Cr_2O_3$, $Fe_2O_3$, floridin, Georgia clay, Gumbrin clay, magnesia (with silica-alumina), molybdenum oxide-alumina, $MoS_2$, $MoS_3$, $MoS_2.CoS$, montmorillonite clay, nickel-alumina, $P_2O_5$, silica-alumina, thoria (with silica-alumina), $ThO_2$(synthetic), $TiO_2$, $WO_3$ (with silica-alumina) and zirconia (with silica-alumina); acidic cation exchanger catalysts such as sulfonated coals, sulfonated phenol-formaldehyde resins, sulfonated divinylbenzene cross linked polymers and exchangers with carboxyl group, phenol group or alumina-silicate skeleton; metathetic cation forming substances such as $AgAsF_6$, $AgClO_4$, $AgBF_4$, $AgNO_3$, $AgOOCCF_3$, $AGPO_4$, $AgPF_6$, $AgSbF_6$, $Ag_2SO_4$, $AgNbF_6$, $AgTaF_6$ and $AgTi_2F_9$; and the mixtures thereof may be used.

Among the above Friedel-Crafts type catalyst acidic halide Lewis acid catalysts, Brønsted acid catalysts, acidic oxide catalysts, metal alkyl Lewis acid catalysts and metal alkoxide acid catalysts are preferably used because they are highly reactive and economical. Particularly, acidic halide Lewis acid catalysts, Brønsted acid catalysts and acidic oxide catalysts are most preferable.

Referring to the amount of such Friedel-Crafts type catalysts, it may be controlled properly according to the kinds of the starting materials, but it is preferable to use them in amounts equimolar with respect to 3-phenylphthalide derivative or more.

As a solvent, benzene, toluene, alkylbenzene, chlorobenzene, dichlorobenzene, bromobenzene, nitrobenzene, alkylnaphthalene, ethylene chloride, chloroform, tetrachloromethane, tetrachloroethane, nitromethane, nitroethane, nitropropane, carbon disulfide, kerosene, high-boiling naphtha, etc. are preferably used. In order to increase the rate of reaction and to minimize the amount of catalyst, it is preferable that such a solvent should not be used or the amount of the solvent should be minimized even when it is used. On the other hand, the excess amount of solvent is preferably used for the purpose of control of the reaction temperature, homogenization of reaction, extraction or the resultant product, etc. Therefore, the solvent should be used as occasion demands.

In this invention, triarylmethane derivatives represented by the general formula (III) or (IV) are obtained by oxidation of the above obtained triarylmethane derivatives represented by the general formula (I) or (II) with use of an oxidizing agent. Triarylmethane derivative represented by the general formula (I) or (II) is dissolved in acidic aqueous solutions such as hydrochloric acid solution and sulfuric acid solution, alkaline aqueous solutions such as caustic soda solution and caustic potash solution, or organic solvents such as alcohols, lower aliphatic carboxylic acids, ethers, ketones, aromatic hydrocarbons, and thereafter an oxidizing agent is added to the solution, and then the oxidation is carried out at the temperature of 0° to 500° C. for the period between several minutes and several decades of hours.

As an oxidizing agent, manganese compounds such as permanganates, manganates, managanese dioxide, manganese(III) salts and manganese acetate; chromic acid compounds such as chromic anhydride, chromic acid, perchromates, alkyl esters of chromic acid and chromyl chloride; lead compounds such as PbO, $PbO_2$ and $Pb(OCOCH_3)_4$; copper compounds such as CuO, $Cu(OH)_2$, $CuSO_4$, $Cu(OCOCH_3)_2$, $CuCl_2$ and $CuBr_2$; cobalt compounds such as $Co_2(SO_4)_3$ and $Co_3O_4$; cerium compounds such as $CeO_2$, $Ce(SO_4)_2$ and $Ce(SO_4)_3$; bismuth compounds such as $Na BiO_3$, BiO and $Bi(OCOCH_3)_2$; silver compounds such as $Ag_2O$, $AgOCOCH_3$ and $AgNO_3$; iron compounds such as $FeCl_3$, $Fe_2(SO_4)_3$ and potassium ferricyanate; $SeO_2$; $RuO_4$; $OsO_4$; inorganic peroxides such as hydrogen peroxide, Fenton's reagent, persulfuric acid and salts thereof; organic peroxides such as performic acid, peracetic acid, perpropionic acid, perbutyric acid, perbenzoic acid, monoperphthalic acid, monoperterephthalic acid, monopersuccinic acid and trifluoroperacetic acid; halides such as hypochlorites, chlorates, hypobromites and bromates; oxygen; ozone; ultraviolet ray; sulfoxides; amine oxides; and chloranil are preferably used. The amount of oxidizing agent may be controlled according to the kinds of oxidizing agent to be used, but it may be usually used in an excess of a stoichiometric amount based on the amount of said triarylmethane derivatives having the general formula (I) or (II).

When the compounds having an oxidizing function such as $FeCl_3$, $FeBr_3$, $AgNO_3$, $CuCl_2$ and peracetic acid are used as a Friedel-Crafts type catalyst in the preparation of triarylmethane derivatives represented by the general formula (I) or (II) from 3-phenylphthalide derivatives and aniline derivatives or indole derivatives, the resultant triarylmethane derivatives represented by the general formula (I) or (II) are instantaneously oxidized to form triarylmethane derivatives represented by the general formula (III) or (IV).

Namely, the reaction of a 3-phenylphthalide derivative with an aniline derivative or an indole derivative to form a triarylmethane derivative having the general formula (I) or (II) is immediately followed by and concurrently occurs with the oxidizing reaction to form said triarylmethane derivative having the general formula (III) or (IV). For this purpose Friedel-Crafts type catalysts may preferably be used in an excess of the total amount of an equimolar amount with respect to said 3-phenylphthalide derivative and a stoichiometric amount based on the amount of said triarylmethane derivative having the general formula (I) or (II)

The process of the invention for the preparation of triarylmethane derivatives from 3-phenylphthalide derivatives is a novel method which has never been described in any literature. The process of the invention gives triarylmethane derivatives at high purities and in extremely high yields. In addition, the process of the invention makes it possible to prepare the various novel triarylmethane derivatives which could not be synthesized by any conventional methods.

The triarylmethane derivatives obtained in this invention form coloured markings upon contact with acidic substances such as solid acids, e.g., acid clay, activated clay, attapulgite, zeolite, kaolin, bentonite and silicates; and organic acidic materials such as phenol-formaldehyde polymers, phenol-acetylene polymers, maleic acid rosin resin, ethylene-maleic acid anhydride polymers, salicylic acid-aldehyde polymers, salicylic acid-acetylene polymers, polyvalent metal salts of those polymers mentioned above, aromatic carboxylic acids, e.g., salicylic acid and salicylic acid derivatives, and polyvalent metal salts of aromatic carboxylic acids by an electron donor-acceptor colour-forming reaction, therefore, they may be utilized as colourless chromogenic compounds (i.e. electron donor) in various fields which utilize such a reaction. For example, triarylmethane derivatives of the invention can be utilized for the production of pressure sensitive copying sheet which is disclosed in U.S. Pat. Nos. 2,730,456 and 2,730,457 and Japanese Pat. No. 511,757, heat sensitive copying sheet which is disclosed in U.S. Pat. Nos. 3,451,338 and 3,539,375, hectographic copying sheet, electron beam sensitive recording sheet, photosensitive sheet, electrographic heat sensitive recording sheet, ultrasonic recording sheet, toner for Xerox type copying sheet, and leuco ink.

PREFERRED EMBODIMENT OF THE INVENTION

The following examples serve to illustrate the invention in more detail although the invention is not limited to the examples.

EXAMPLE 1

30 g of 3-(p-dimethylaminophenyl)-6-dimethylaminophthalide and 13 g of dimethylaniline were dissolved in 250 cc of tetrachloroethane. 14 g of anhydrous aluminum chloride was added to the solution and the resultant mixture was heated at 50° C. for 3 hours with stirring. After the termination of reaction, 30% aqueous solution of caustic soda was added to dissolve aluminum chloride while cooling the mixture with ice. Then, the tetrachloroethane phase was separated with the aid of a separatory funnel, and then stream distilled to remove the unreacted dimethylaniline and tetrachloroethane. The remaining aqueous phase was neutralized with acetic acid to obtain a pale yellow solid. The yield was 42 g. This solid was recrystallized from benzene to obtain colourless crystals having a melting point (hereinafter referred to as m.p.) of 201° C. The obtained crystal results in a blue colouration when it is subjected to light on silica gel. This compound is triarylmethane represented by the following formula:

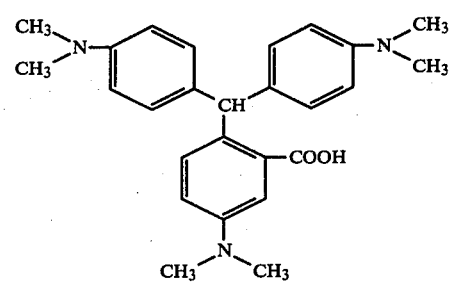

EXAMPLE 2

30 g of 3-(p-dimethylaminophenyl)-6-dimethylaminophthalide and 17 g of N,N-diethyl-m-toluidine were dissolved in 300 cc of benzene. After the addition of 14 g of zinc chloride, the mixture was heated at 80° C. for 5 hours with stirring. After cooling, the resultant precipitate was filtered and then dried. The obtained precipitate was dissolved in dilute hydrochloric acid, and then the pH of the solution was adjusted at 4.0 with an aqueous solution of caustic soda to form a yellow precipitate. This precipitate was filtered and then dried. The yield was 45 g. Recrystallization from benzene gave triarylmethane represented by the following formula in the form of colourless crystals whose m.p. was 255°–260° C. This compound turns in blue colour upon exposure to light on TCL.

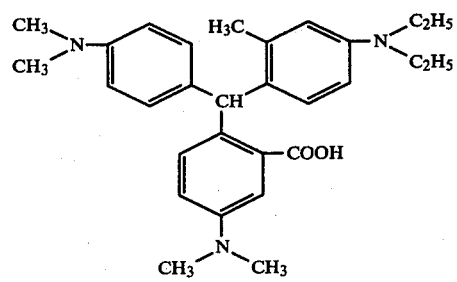

EXAMPLE 3

Example 1 was repeated except that 26 g of 3-(p-dimethylaminophenyl)phthalide was used instead of 30 g of 3-(p-dimethylaminophenyl)-6-dimethylaminophthalide to obtain 32 g of triarylmethane represented by the following formula whose m.p. was 194°–195° C. in the form of colourless crystals. This compound becomes bluish green upon exposure to light on silica gel.

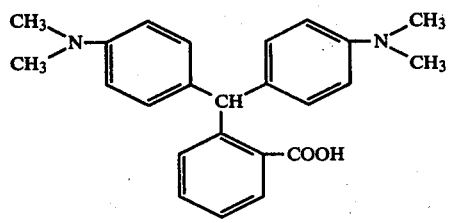

EXAMPLE 4

Example 1 was repeated except that 29 g of 3-(o-methoxyphenyl)-6-dimethylaminophthalide was used instead of 30 g of 3-(p-dimethylaminophenyl)-6-dimethylaminophthalide to obtain 38 g of triarylmethane represented by the following formula whose m.p. was 237°–238° C. in the form of colourless crystals (Recrystallized from acetic acid-methanol). This compound becomes bluish green upon exposure to light on silica gel.

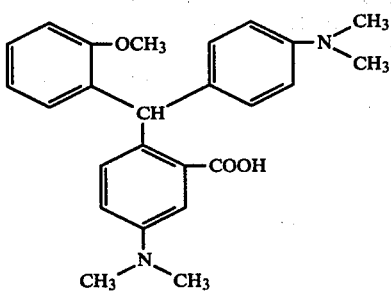

EXAMPLE 5

Example 1 was repeated except that 13.5 g of 2-methylindole was used instead of 13 g of dimethylaniline to obtain 34 g of triarylmethane having the following formula in the form of colourless crystals. This compound becomes violet upon exposure to light on silica gel.

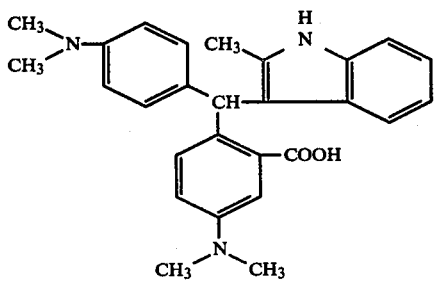

EXAMPLE 6

Example 1 was repeated except that 29 g of 3-(o-methoxyphenyl)-6-dimethylaminophthalide and 13.5 g of 2-methylindole were used instead of 30 g of 3-(p-dimethylaminophenyl)-6-dimethylaminophthalide and 13 g of dimethylaniline, respectively, to obtain 29 g of triarylmethane having the following structure whose m.p. was 203°–205° C. in the form of colourless crystals (Recrystallized from methanol). This compound becomes blue black upon exposure to light on silica gel.

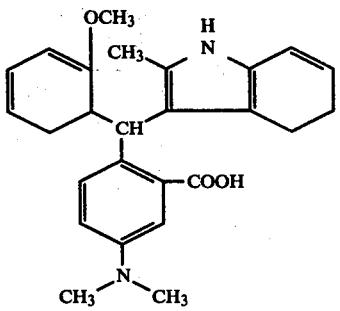

EXAMPLE 7

Example 1 was repeated except that 32 g of 3-(3',4'-dimethoxyphenyl)-6-dimethylaminophthalide and 13.5 g of 2-methylindole were used, respectively, instead of 30 g of 3-(p-dimethylaminophenyl)-6-dimethylaminophthalide and 13 g of dimethylaniline to obtain 33 g of triarylmethane having the following structure whose m.p. was 230°–232° C. in the form of colourless crystals (Recrystallized from methanol). This compound becomes bluish violet upon exposure to light on silica gel.

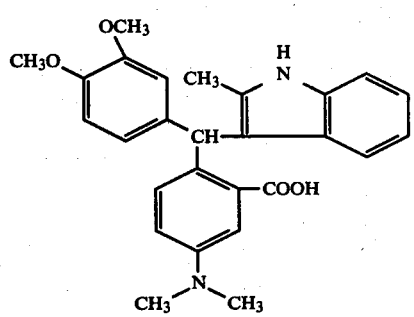

EXAMPLE 8

Example 1 was repeated except that 19.5 g of 2-phenylindole was used instead of 13 g of dimethylaniline to obtain 34 g of triarylmethane having the following structure in the form of colourless crystals. This compound becomes blue upon exposure to light on silica gel.

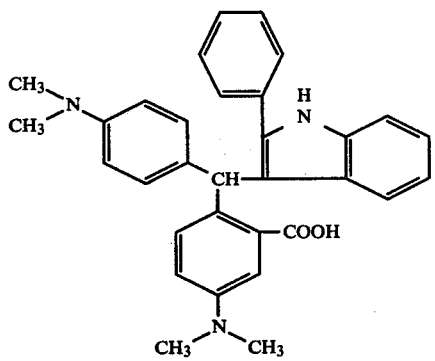

EXAMPLE 9

Example 1 was repeated except that 32 g of 3-(2',4'-dimethoxyphenyl)-6-dimethylaminophthalide and 13.5 g of 2-methylindole were used, respectively, instead of 30 g of 3-(p-dimethylaminophenyl)-6-dimethylaminophthalide and 13 g of dimethylaniline to obtain 27 g of triarylmethane having the following structure whose m.p. was 202°–203° C. in the form of colourless crystals (Recrystallized from methanol). This compound becomes bluish violet upon exposure to light on silica gel.

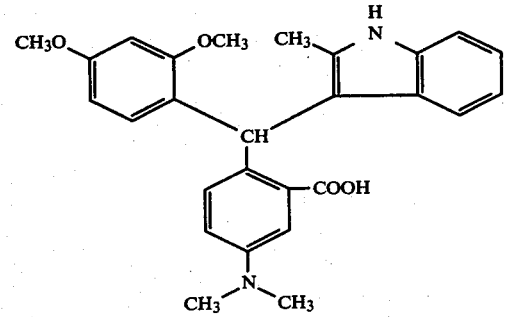

EXAMPLE 10

Example 1 was repeated except that 30 g of 3-(p-dimethylaminophenyl)-6-ethoxyphthalide was used instead of 30 g of 3-(p-dimethylaminophenyl)-6-dimethylaminophthalide to obtain 39 g of triarylmethane having the following structure whose m.p. was 197°–198° C. in the form of colourless crystals. This compound becomes bluish green upon exposure to light on silica gel.

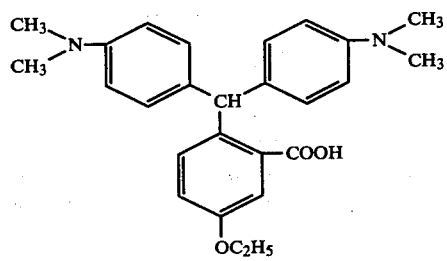

EXAMPLE 11

Example 1 was repeated with use of the various starting materials and catalysts shown in the following table instead of 3-(p-dimethylaminophenyl)-6-dimethylaminophthalide, dimethylaniline and anhydrous aluminum chloride to obtain the various triarylmethane compounds shown in the following table. The colours formed upon exposure to light on silica gel are shown in the following table as well.

| 3-phenylphthalide derivatives | aniline or indole derivatives | catalysts | resultant compounds | color |
|---|---|---|---|---|
| [C₂H₅,(C₂H₅)N–C₆H₄–CH–C₆H₄–N(CH₃)(CH₃); O–C=O] | (C₂H₅)₂N–C₆H₅ | ZnCl₂ | [(C₂H₅)₂N–C₆H₄–CH(–C₆H₄–N(C₂H₅)₂)–C₆H₃(COOH)(N(CH₃)₂)] | Blue |
| [(CH₃)₂N–C₆H₄–CH–C₆H₄–N(C₄H₉)(C₄H₉); O–C=O] | (CH₃)₂N–C₆H₅ | " | [(CH₃)₂N–C₆H₄–CH(–C₆H₄–N(CH₃)₂)–C₆H₃(COOH)(N(C₄H₉)₂)] | " |
| [(CH₃)₂N–C₆H₄–CH–C₆H₄–N(CH₃)(CH₂C₆H₅); O–C=O] | " | " | [(CH₃)₂N–C₆H₄–CH(–C₆H₄–N(CH₃)₂)–C₆H₃(COOH)(N(CH₃)(CH₂C₆H₅))] | " |

-continued

| 3-phenylphthalide derivatives | aniline or indole derivatives | catalysts | resultant compounds | color |
|---|---|---|---|---|
| [structure: 3-phenylphthalide with two N(CH3)2 groups and N(CH3)(tolyl) substituent] | " | " | [structure: triarylmethane with COOH, two N(CH3)2 and N(CH3)(p-tolyl)] | " |
| [structure: 3-phenylphthalide with N(CH3)2 and piperidinyl] | " | " | [structure: triarylmethane with COOH, two N(CH3)2 and piperidinyl] | " |
| [structure: 3-phenylphthalide with two N(CH3)2 and Cl] | " | Ti(i-PrO)4 | [structure: triarylmethane with COOH, two N(CH3)2, Cl and N(CH3)2] | " |
| [structure: 3-phenylphthalide with N(CH3)2 and Cl] | " | SiO2—Al2O3 | [structure: triarylmethane with COOH, two N(CH3)2 and Cl] | Bluish green |
| [structure: 3-phenylphthalide with N(CH3)2 and two Br] | " | " | [structure: triarylmethane with COOH, two N(CH3)2 and two Br] | Bluish green |
| [structure: 3-phenylphthalide with N(C2H5)2, CH3 substituents] | [structure: m-phenylenediamine bis-N(CH3)2] | ZnCl2 | [structure: triarylmethane with COOH, N(C2H5)2, CH3, and two N(CH3)2 groups] | Blue black |

-continued

| 3-phenylphthalide derivatives | aniline or indole derivatives | catalysts | resultant compounds | color |
|---|---|---|---|---|
| [structure: 4-dimethylamino, 4-nitro phenylphthalide] | N,N-dimethylaniline | " | [structure: bis(4-dimethylamino)phenyl methane with COOH and NO2] | Bluish green |
| [structure: bis(4-dimethylamino) phenylphthalide] | CH3,C12H25-N-phenyl | Al(C2H5)3 | [structure with C12H25 and N(CH3)2 groups, COOH] | Blue |
| [structure: bis(4-dimethylamino) phenylphthalide] | 1,8-bis(dimethylamino)naphthalene isopropyl | ZnCl2 | [structure with naphthalene diamine group, COOH, N(CH3)2] | Blue black |
| [structure: bis(4-dimethylamino) phenylphthalide] | N,N-dimethylaniline | " | [structure with two N(CH3)2, COOH, N(CH3)2] | Bluish green |
| [structure: bis(4-dimethylamino) phenylphthalide] | N-methylaniline | CH3COOH | [structure with NHCH3, N(CH3)2, COOH] | Blue |
| [structure: bis(4-dimethylamino) phenylphthalide] | 3-chloro-N,N-dimethylaniline | CF3COOH | [structure with Cl, two N(CH3)2, COOH] | " |

| 3-phenylphthalide derivatives | aniline or indole derivatives | catalysts | resultant compounds | color |
|---|---|---|---|---|
| (structure) | (structure) | SiO₂ | (structure) | " |
| (structure) | (structure) | Clay(acid activated) | (structure) | Blue |

EXAMPLE 12

Example 1 was repeated except that 33 g of anhydrous ferric chloride was used instead of 14 g of anhydrous aluminum chloride to obtain 16 g of compound having the following structure whose m.p. was 180° C. in the form of colourless crystals (Recrystallized from benzene-methanol). This compound becomes blue upon contact with silica gel.

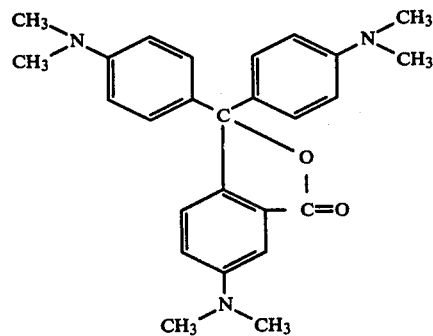

EXAMPLE 13

Example 12 was repeated with use of the various starting materials and catalysts shown in the following table instead of 3-(p-dimethylaminophenyl)-6-dimethylaminophthalide, dimethylaniline and anhydrous ferric chloride to obtain the various triarylmethane compounds shown in the following table. Those compounds produce the various colours shown in the following table immediately upon contact with silica gel.

| 3-phenylphthalide derivatives | aniline or indole derivatives | catalysts | resultant compounds | color |
|---|---|---|---|---|
| (structure) | (structure) | FeBr₃ | (structure) | Blue |

| 3-phenylphthalide derivatives | aniline or indole derivatives | catalysts | resultant compounds | color |
|---|---|---|---|---|
| (CH₃)₂N–C₆H₄–CH(–C₆H₃(N(CH₃)₂))–O–C=O | C₃H₇–N(C₃H₇)–C₆H₅ | CuCl₂ | (CH₃)₂N–C₆H₄–C(–C₆H₄–N(C₃H₇)₂)(–C₆H₃(N(CH₃)₂)–C(=O)–O–) | " |
| (C₂H₅)₂N–C₆H₃(CH₃)–CH(–C₆H₃(N(CH₃)₂))–O–C=O | (C₂H₅)₂N–C₆H₄–CH₃ | FeCl₃ | (C₂H₅)₂N–C₆H₃(CH₃)–C(–C₆H₃(CH₃)–N(C₂H₅)₂)(–C₆H₃(N(CH₃)₂)–C(=O)–O–) | " |
| (C₂H₅)₂N–C₆H₄–CH(–C₆H₂(Cl)(N(CH₃)₂))–O–C=O | 1,2-dimethylindole | AgNO₃ | (C₂H₅)₂N–C₆H₄–C(–indolyl(CH₃,C₂H₅))(–C₆H₂(Cl)(N(CH₃)₂)–C(=O)–O–) | Violet |

EXAMPLE 14

33 g of 3-(m-diethylaminophenyl)-6-dimethylaminophthalide and 13 g of dimethylaniline were dissolved in 300 cc of tetrachloroethane. 14 g of anhydrous aluminum chloride was added to the solution, and then the mixture was heated at 50° C. for 3 hours with stirring. After the termination of reaction, 30% aqueous solution of caustic soda was added to the mixture to dissolve aluminum chloride while cooling with ice. Tetrachloroethane phase was steam distilled to remove unreacted dimethylaniline and tetrachloroethane. The remaining aqueous phase was neutralized with acetic acid to obtain a white solid. This solid was dissolved in 600 cc of 2.5% aqueous solution of caustic soda, and then heated at 50° C. 600 cc of 5% aqueous solution of potassium persulfate was added dropwise to the above solution, and then the mixture was heated at 60° C. for 3 hours. After the termination of reaction, the resultant precipitates were filtered and recrystallized from methanol to obtain 31 g of 3-(m-diethylaminophenyl)-3-(p-dimethylaminophenyl)-6-dimethylaminophthalide having the following structure whose m.p. was 177°–178° C. in the form of colourless crystals. This compound become green on contact with silica gel.

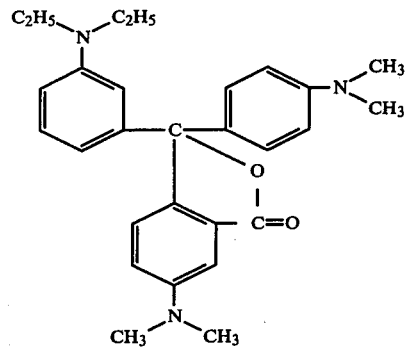

EXAMPLE 15

Example 14 was repeated except that 29 g of 3-(p-methoxyphenyl)-6-dimethylaminophthalide and 19.5 g of 2-phenylindole were used, respectively, instead of 33 g of 3-(m-diethylaminophenyl)-6-dimethylaminophthalide and 13 g of dimethylaniline to obtain 24 g of 3-(p-methoxyphenyl)-3-(2-phenylindole-3-yl)-6-dimethylaminophthalide having the following structure whose m.p. was 224°–225° C. in the form of colourless crystals (Recrystallized from benzene-methanol). This compound becomes blue black on contact with silica gel.

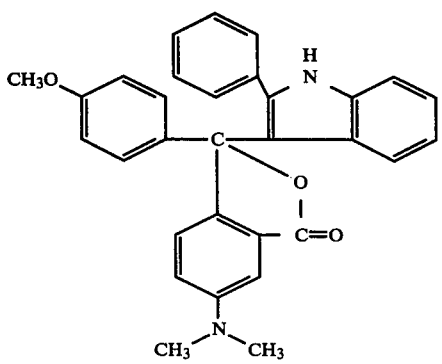

EXAMPLE 16

Example 14 was repeated except that 32 g of 3-(3,4-dimetoxyphenyl)-6-dimethylaminophthalide and 19.5 g of 2-phenylindole were used instead of 33 g of 3-(m-diethylaminophenyl)-6-dimethylaminophthalide and 13 g of dimethylaniline to obtain 21 g of 3-(3',4'-dimetoxyphenyl)-3(2'-phenylindole-3'-yl)-6-dimethylaminophthalide having the following structure whose m.p. was 235°–236° C. in the form of colourless crystals (Recrystallized from benzene-methanol). This compound becomes blue black upon contact with silica gel.

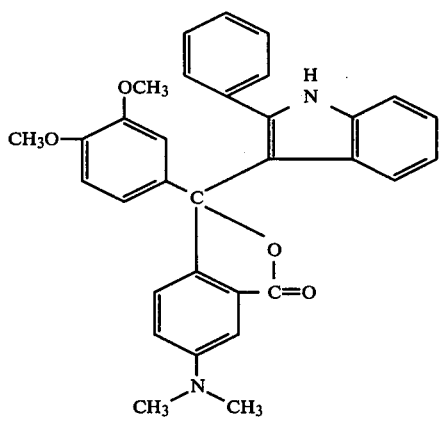

EXAMPLE 17

Example 14 was repeated except that 32 g of 3-(2',4'-dimethoxyphenyl)-6-dimethylaminophthalide and 19.5 g of 2-phenylindole were used instead of 33 g of 3-(m-diethylaminophenyl)-6-dimethylaminophthalide and 13 g of dimethylaniline to obtain 30 g of 3-(2',4'-dimethoxyphenyl)-3-(2'-phenylindole-3'-yl)-6-dimethylaminophthalide having the following structure whose m.p. was 239°–240° C. in the form of colourless crystals (Recrystallized from benzene-methanol). This compound becomes blue black upon contact with silica gel.

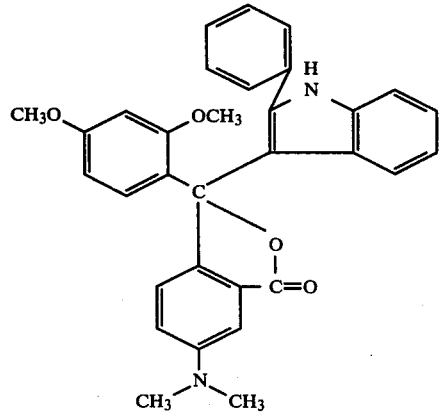

EXAMPLE 18

Example 14 was repeated except that 35 g of 3-(juloidine-6'-yl)phthalide, and 15 g of 1,2-dimethylindole were used instead of 33 g of 3-(m-diethylaminophenyl)-6-dimethylaminophthalide and 13 g of dimethylaniline to obtain 28 g of 3-(juloidine-6'-yl)-3-(1',2'-dimethylindole-3'-yl)phthalide having the following structure whose m.p. was 259°–260° C. in the form of colourless crystals (Recrystallized from alcohol). This compound becomes violet upon contact with silica gel.

EXAMPLE 19

Example 14 was repeated except that 38 g of 3-{p-di(n-butyl)aminophenyl}phthalide and 15 g of 1,2-dimethylindole were used instead of 33 g of 3-(m-diethylaminophenyl)-6-dimethylaminophthalide and 13 g of dimethylaniline to obtain 33 g of 3-{p-di(n-butyl)aminophenyl}-3-(1',2'-dimethylindole-3'-yl)phthalide having the following structure whose m.p. was 140°–142° C. in the form of colourless crystals (Recrystallized from benzene-methanol). This compound becomes violet on contact with silica gel.

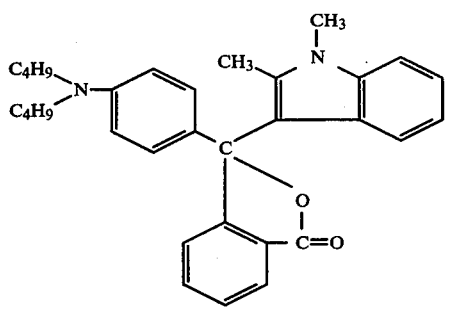

EXAMPLE 20

Example 14 was repeated with use of the following various 3-phenylphthalide derivatives instead of 3-(m-diethylaminophenyl)-6-dimethylaminophthalide, and the following various aniline or indole derivatives instead of dimethylaniline to obtain the triarylmethane derivatives shown in the following table. The colours which were formed on contact with silica gel are shown in the following table as well.

| 3-phenylphthalide derivatives | aniline or indole derivatives | resultant compound | m.p. | color |
|---|---|---|---|---|
| (structure) | (structure) | (structure) | 89–93° C. | Blue |
| " | (structure) | (structure) | 147–149° C. | " |
| " | (structure) | (structure) | 187–189° C. | " |

-continued
| 3-phenylphthalide derivatives | aniline or indole derivatives | resultant compound | m.p. | color |
|---|---|---|---|---|
| " | 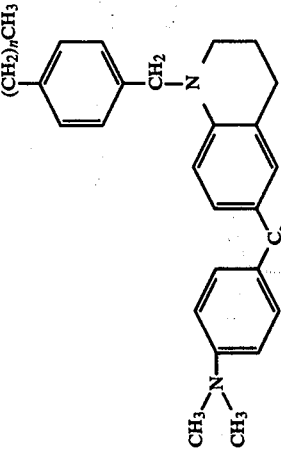 | 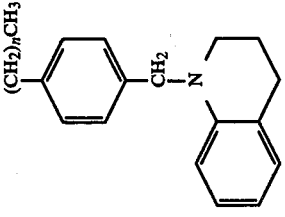 | 68–70° C. | " |
| " |  | 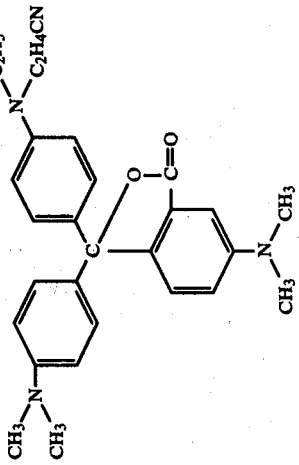 | — | " |

-continued

| 3-phenylphthalide derivatives | aniline or indole derivatives | resultant compound | m.p. | color |
|---|---|---|---|---|
| " | C₂H₅—N(C₆H₅)—C₂H₄OH | [structure with N(C₂H₅)(C₂H₄OH) and N(CH₃)₂ and N(CH₃)₂] | — | " |
| " | C₆H₅—N(CH₂C₆H₅)—C₂H₅ | [structure with N(C₂H₅)(CH₂C₆H₅) and N(CH₃)₂ and N(CH₃)₂] | 143–145° C. | " |
| " | 1-(phenylamino)naphthalene | [structure with NHC₆H₅-naphthyl and N(CH₃)₂ and N(CH₃)₂] | — | Green |

-continued

| 3-phenylphthalide derivatives | aniline or indole derivatives | resultant compound | m.p. | color |
|---|---|---|---|---|
| " | N,N-di(allyl)aniline | [structure] | — | Blue |
| " | N,N-di(propargyl)aniline | [structure] | — | " |
| " | N-phenylpiperidine | [structure] | — | " |

| 3-phenylphthalide derivatives | aniline or indole derivatives | resultant compound | m.p. | color |
|---|---|---|---|---|
| " | (cyclohexyl-N-CH₃-phenyl) | [triarylmethane lactone with cyclohexyl-N-CH₃ and two p-N(CH₃)₂ groups] | — | " |
| [3-(4-nitrophenyl)-6-dimethylaminophthalide] | (N,N-dimethylaniline) | [triarylmethane lactone with p-NO₂-phenyl, p-N(CH₃)₂-phenyl, and dimethylamino group] | — | Bluish green |
| [3-(2-chlorophenyl)-6-dimethylaminophthalide] | " | [triarylmethane lactone with o-Cl-phenyl, p-N(CH₃)₂-phenyl, and dimethylamino group] | — | Bluish green |

| 3-phenylphthalide derivatives | aniline or indole derivatives | resultant compound | m.p. | color |
|---|---|---|---|---|
| 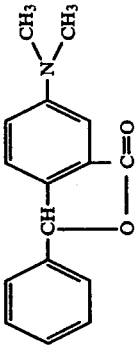 | | 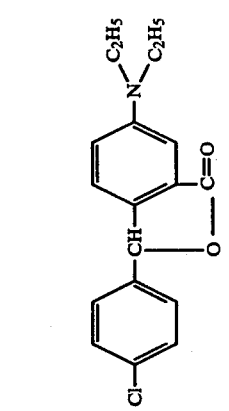 | — | Bluish green |
| 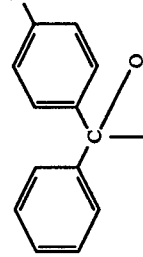 | 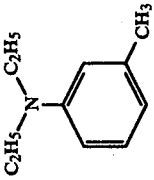 | 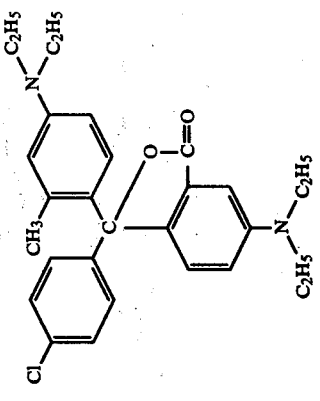 | — | Bluish green |
| 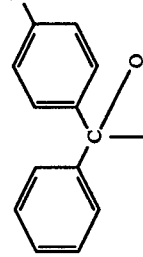 | 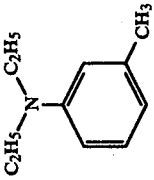 | 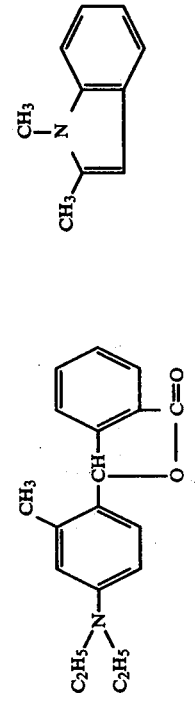 | 180–182° C. | Blue |

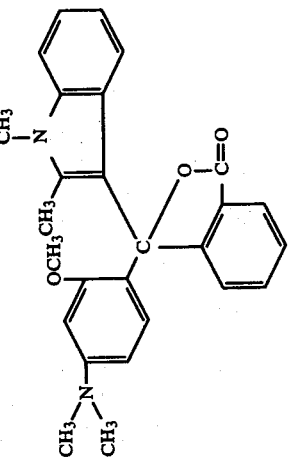

-continued

| 3-phenylphthalide derivatives | aniline or indole derivatives | resultant compound | m.p. | color |
|---|---|---|---|---|
| (structure with OCH₃, CH₃NH substituents) | 1,2-dimethylindole (CH₃-N, CH₃) | (phthalide adduct) | 200–202° C. | " |
| (structure with OC₂H₅, (C₂H₅)₂N substituents) | 2-methylindole (H-N, CH₃) | (phthalide adduct) | 223–225° C. | blue |
| (structure with morpholino substituent) | 1,2-dimethylindole (CH₃-N, CH₃) | (phthalide adduct) | 238–239° C. | reddish violet |

-continued

| 3-phenylphthalide derivatives | aniline or indole derivatives | resultant compound | m.p. | color |
|---|---|---|---|---|
| (structure) | (structure) | (structure) | 242–243° C. | reddish violet |
| (structure) | (structure) | (structure) | 95–98° C. | violet |
| (structure) | (structure) | (structure) | 102–105° C. | bluish green |

-continued

| 3-phenylphthalide derivatives | aniline or indole derivatives | resultant compound | m.p. | color |
|---|---|---|---|---|
| (structure) | (structure) | (structure) | 125–128° C. | bluish green |
| (structure) | (structure) | (structure) | 263–265° C. | blue black |

-continued

| 3-phenylphthalide derivatives | aniline or indole derivatives | resultant compound | m.p. | color |
|---|---|---|---|---|
| | | | 235–237° C. | green |
| " | | | 220–223° C. | blue |

-continued

| 3-phenylphthalide derivatives | aniline or indole derivatives | resultant compound | m.p. | color |
|---|---|---|---|---|
| (structure) | (structure) | (structure) | — | violet |
| | (structure) | (structure) | — | " |

-continued
| 3-phenylphthalide derivatives | aniline or indole derivatives | resultant compound | m.p. | color |
|---|---|---|---|---|
| " | 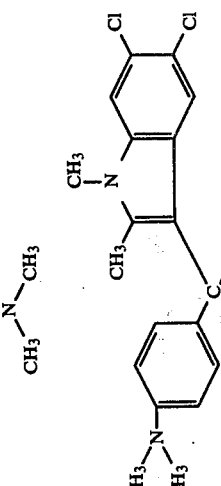 | 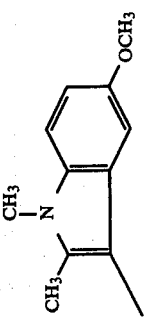 | — | " |
| 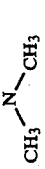 | 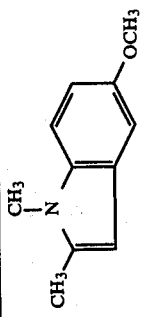 | 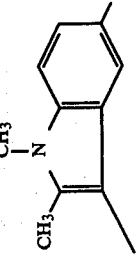 | — | violet |

EXAMPLE 21

10 g of the triarylmethane derivative obtained in Example 2 was dissolved in 100 cc of ethylene glycol monomethyl ether. 7 g of chloranil was added to the solution, and then the mixture was heated at 50° C. for one hour with stirring. The reaction mixture was poured into 2000 cc of water. After the adjustment of the pH of the mixture solution at less than 2 with dilute hydrochloric acid, the insoluble material was removed by filtration. The pH of the filtrate was adjusted at 4 with an aqueous solution of caustic soda to obtain a pale blue solid. After drying, the solid was recrystallized from benzenemethanol to obtain 3-(p-dimethylaminophenyl)-3-(2'-methyl-4'-diethylaminophenyl)-6-dimethylaminophthalide having the following structure whose m.p. was 212°–214° C. in the form of colourless crystals. This compound immediately becomes blue on contact with silica gel.

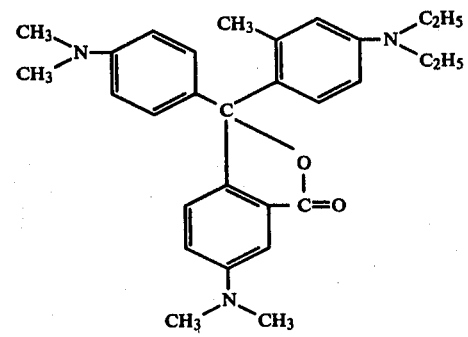

EXAMPLE 22

Example 21 was repeated with use of the various triarylmethane derivatives obtained in Examples 3 to 11 and the various oxidizing agents and solvents as shown in the following table to prepare the various triarylmethane lactone derivatives. The colours which were formed on silica gel are shown in the following table as well.

| triarylmethane derivatives | solvents | oxidizing agents | resultant compounds | m.p. | color |
|---|---|---|---|---|---|
| 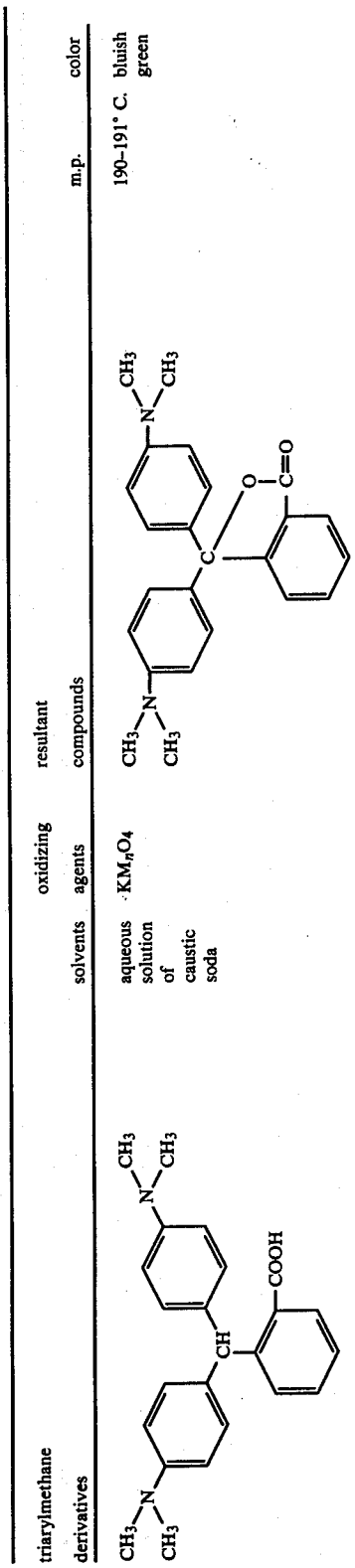 | aqueous solution of caustic soda | KMnO4 | | 190–191° C. | bluish green |
| 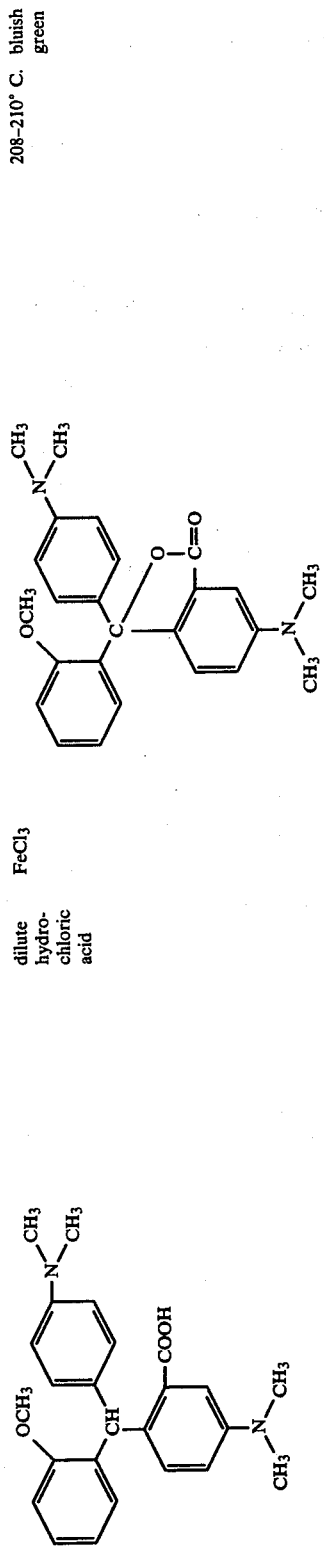 | dilute hydrochloric acid | FeCl3 | | 208–210° C. | bluish green |
| 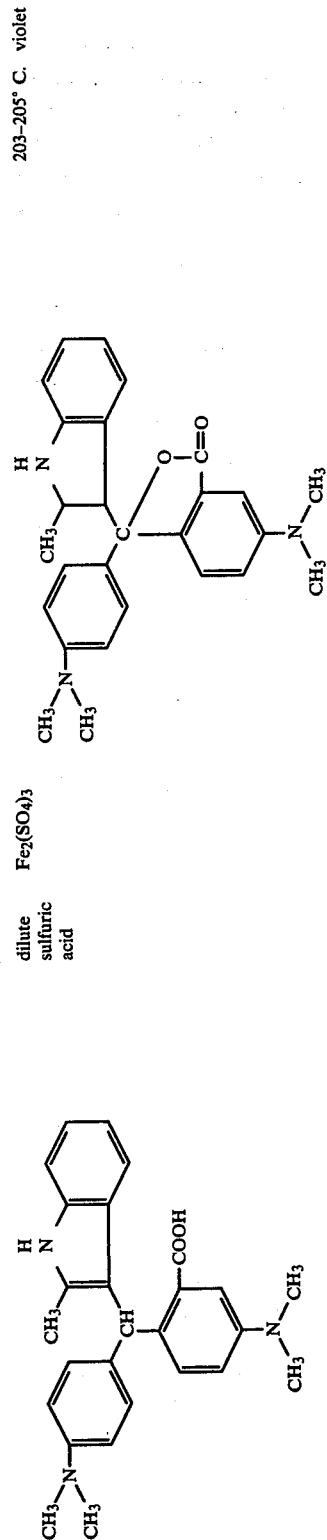 | dilute sulfuric acid | Fe2(SO4)3 | | 203–205° C. | violet |

-continued
| triarylmethane derivatives | solvents | oxidizing agents | resultant compounds | m.p. | color |
|---|---|---|---|---|---|
| 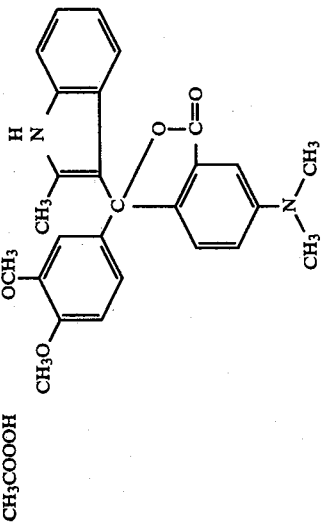 | aqueous solution of caustic soda | NaClO | 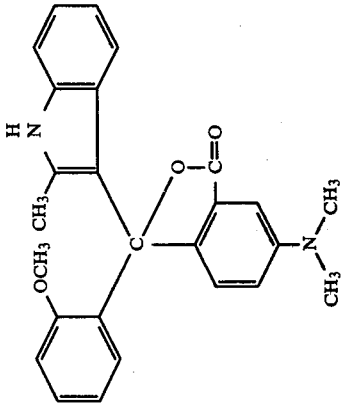 | 235–236° C. | blue black |
| 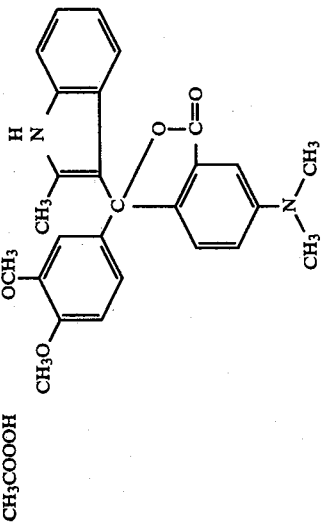 | acetic acid | CH₃COOOH | 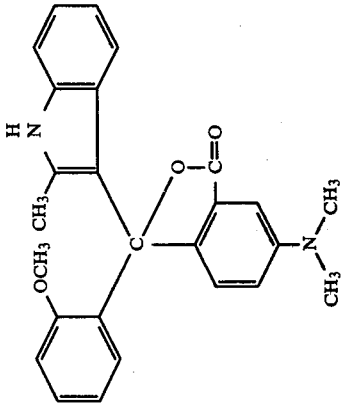 | 244–245° C. | bluish violet |

-continued

| triarylmethane derivatives | solvents | oxidizing agents | resultant compounds | m.p. | color |
|---|---|---|---|---|---|
| [structure] | aqueous solution of caustic soda | AgNO₃ | [structure] | 252–253° C. | blue |
| [structure] | dilute hydrochloric acid | PbO₂ | [structure] | 213–215° C. | bluish violet |
| [structure] | aqueous solution of caustic soda | K₂S₂O₈ | [structure] | 167–168° C. | bluish green |

| triarylmethane derivatives | solvents | oxidizing agents | resultant compounds | m.p. | color |
|---|---|---|---|---|---|
| [structure: bis(4-diethylamino)phenyl-CH with 2-COOH-5-(N-methyl-N-methyl)aminophenyl] | dilute hydrochloric acid | PbO₂ | [structure: corresponding lactone with diethylamino groups] | 172–175° C. | blue |
| [structure: bis(4-dimethylamino)phenyl-CH with 2-COOH-5-(N-butyl-N-methyl)aminophenyl] | dilute hydrochloric acid | PbO₂ | [structure: corresponding lactone] | 80–85° C. | blue |
| [structure: bis(4-dimethylamino)phenyl-CH with 2-COOH-5-(N-methyl-N-benzyl)aminophenyl] | dilute hydrochloric acid | CuCl₂ | [structure: corresponding lactone] | — | blue |

-continued

| triarylmethane derivatives | solvents | oxidizing agents | resultant compounds | m.p. | color |
|---|---|---|---|---|---|
| [structure] | aqueous solution of caustic soda | Na$_2$S$_2$O$_8$ | [structure] | — | blue |
| [structure] | aqueous solution of caustic soda | Na$_2$S$_2$O$_8$ | [structure] | — | blue |
| [structure] | aqueous solution of caustic soda | Na$_2$S$_2$O$_8$ | [structure] | — | blue |

| triarylmethane derivatives | solvents | oxidizing agents | resultant compounds | m.p. | color |
|---|---|---|---|---|---|
| 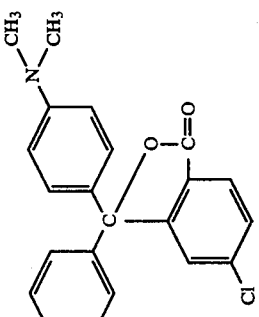 | dilute sulfuric acid | K₂Cr₂O₇ | 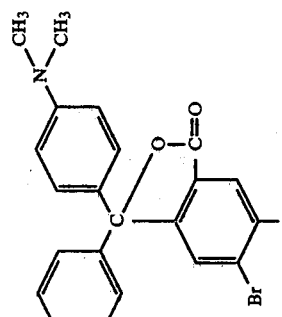 | 186–187° C. | bluish green |
| 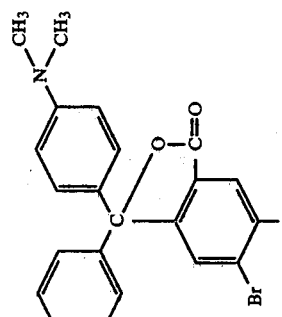 | aqueous solution of caustic soda | H₂O₂ | 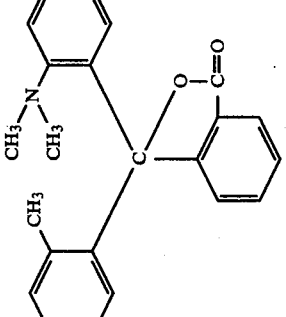 | 218° C. | bluish green |
| 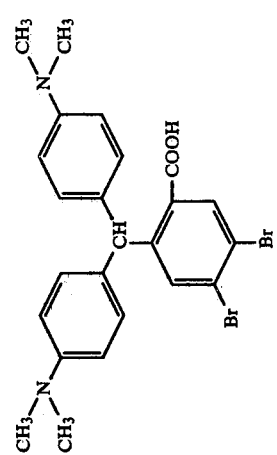 | aqueous solution of caustic soda | H₂O₂ | 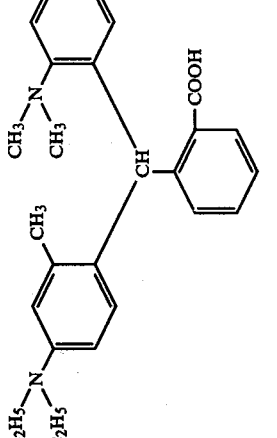 | 204–206° C. | blue black |

-continued

| triarylmethane derivatives | solvents | oxidizing agents | resultant compounds | m.p. | color |
|---|---|---|---|---|---|
| (structure: bis(4-dimethylaminophenyl)methane with 2-COOH-4-NO₂-phenyl group) | aqueous solution of caustic soda | H₂O₂ | (corresponding triarylmethane lactone with NO₂) | — | bluish green |
| (structure: bis(4-dimethylaminophenyl)methane with 2-COOH-4-(N-methyl-N-dodecylamino)phenyl group) | aqueous solution of caustic soda | H₂O₂ | (corresponding lactone) | viscous solid | blue |
| (structure: naphthalene-bridged bis(dimethylamino) with bis(4-dimethylaminophenyl)methane and 2-COOH-4-dimethylaminophenyl group) | aqueous solution of caustic soda | H₂O₂ | (corresponding lactone) | — | blue black |

-continued

| triarylmethane derivatives | solvents | oxidizing agents | resultant compounds | m.p. | color |
|---|---|---|---|---|---|
| (structure) | ethylene glycol monomethyl ether | chloranil | (structure) | 151–152° C. | bluish green |
| (structure) | ethylene glycol monomethyl ether | chloranil | (structure) | 183–186° C. | blue |
| (structure) | aqueous solution of caustic soda | $K_2S_2O_8$ | (structure) | — | blue |

-continued

| triarylmethane derivatives | solvents | oxidizing agents | resultant compounds | m.p. | color |
|---|---|---|---|---|---|
| [structure with OCH₃, N(C₂H₅)₂, N(CH₃)₂, COOH, N(CH₃)₂ groups] | aqueous solution of caustic soda | K₂S₂O₈ | [triarylmethane lactone structure with OCH₃, N(C₂H₅)₂, N(CH₃)₂, C=O, O, N(CH₃)₂ groups] | — | blue |
| [structure with SCH₃, Cl, N(CH₃)₂, N(CH₃)₂, COOH, N(CH₃)₂ groups] | aqueous solution of caustic soda | K₂S₂O₈ | [triarylmethane lactone structure with SCH₃, Cl, N(CH₃)₂, N(CH₃)₂, C=O, O, N(CH₃)₂ groups] | — | blue |

What we claim is:

1. A process for preparing a triarylmethane derivative having the structural formula

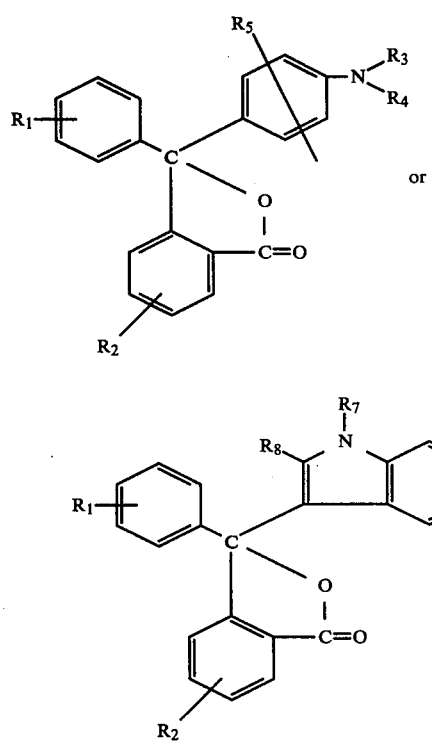

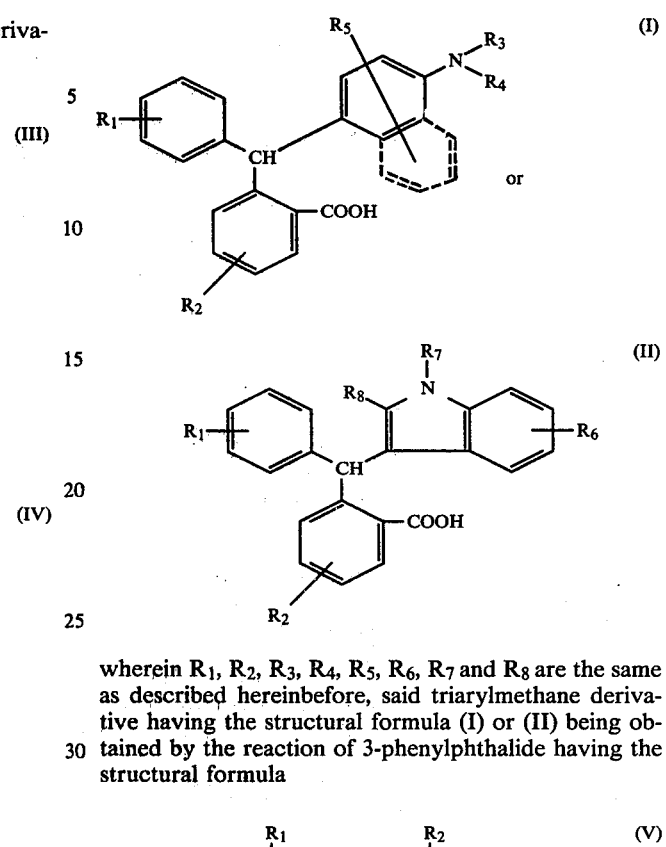

wherein each $R_1$ and $R_2$ represents at least one of hydrogen, halogen, nitro group, alkyl group, amino group, alkyl-, benzyl-, phenyl-, tolyl-, or pentylene-substituted amino group, hydroxyl group, alkyl-substituted hydroxyl group, thiohydroxyl group or alkyl-substituted thiohydroxyl group, each $R_3$ and $R_4$ represents hydrogen, cyano-, hydroxyl-, halogen-, methoxy-, ethoxy-, or ethoxycarbonyl-substituted or unsubstituted alkyl group, cycloalkyl group, alkyl-substituted or unsubstituted aralkyl group, aryl group, or unsaturated alkyl group, or one or both of $R_3$ and $R_4$ together with the adjacent nitrogen atom may form a morpholine ring, a pyrrolidine ring, a pyrazolidine ring, a piperidine ring, an imidazoline ring, a piperazine ring, or a pyrimidine ring, $R_5$ represents at least one of hydrogen, halogen, alkyl group, nitro group, lower alkyl-substituted or unsubstituted amino group, lower alkyl-substituted or unsubstituted hydroxyl group, or lower alkyl-substituted or unsubstituted thiohydroxyl group, $R_6$ represents at least one of hydrogen, halogen, lower alkyl group, lower alkoxyl group, amino group, lower alkylamino group, nitro group, phenyl group or phenoxy group, $R_7$ represents hydrogen, alkyl group, aralkyl group or phenyl group, $R_8$ represents an alkyl group or alkyl-, halogen-, or alkoxy-substituted or unsubstituted phenyl group which comprises oxidizing a triarylmethane derivative having the structural formula wherein $R_1$, $R_2$, $R_3$, $R_4$, $R_5$, $R_6$, $R_7$ and $R_8$ are the same as described hereinbefore, said triarylmethane derivative having the structural formula (I) or (II) being obtained by the reaction of 3-phenylphthalide having the structural formula

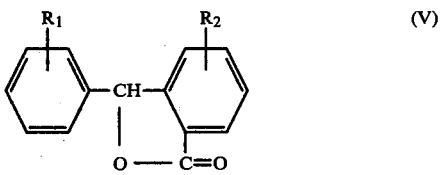

wherein $R_1$ and $R_2$ are the same as described hereinbefore with the aniline derivative having the structural formula

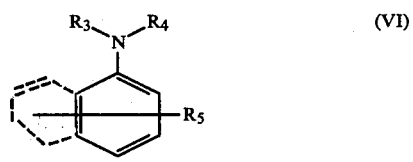

wherein $R_3$, $R_4$ and $R_5$ are the same as described hereinbefore, or with the indole derivative having the structural formula wherein $R_6$, $R_7$ and $R_8$ are the same as described hereinbefore in the presence of a Friedel-Crafts type catalyst.

2. A process for preparing triarylmethane derivative as defined in claim 1, wherein said 3-phenylphthalide derivatives having the structural formula (V) has $R_2$ at the 6 position.

3. A process for preparing triarylmethane derivative as defined in claim 2, wherein said $R_2$ is at least one alkyl-, benzyl-, phenyl-, tolyl-, or pentylene-substituted amino group.

4. A process for preparing triarylmethane derivative as defined in claim 1, wherein said Friedel-Crafts type catalyst comprises at least one member selected from the group consisting of acidic halide Lewis acid catalysts, Brφnsted acid catalysts, acidic oxide catalysts, metal alkyl Lewis acid catalysts and metal alkoxide Lewis acid catalysts.

5. A process for preparing triarylmethane derivative as defined in claim 4, wherein said Friedel-Crafts type catalyst comprises at least one member selected from the group consisting of acidic halide Lewis acid catalysts, Brφnsted acid catalysts and acidic oxide catalysts.

6. A process for preparing triarylmethane derivative as defined in claim 1, wherein said Friedel-Crafts type catalyst is used in an equimolar amount with respect to said 3-phenylphthalide derivative or more.

7. A process for preparing triarylmethane derivative as defined in claim 1, wherein the reaction of said 3-phenylphthalide derivative with said aniline derivative or said indole derivative is carried out a temperature within the range of 0° to 180° C.

8. A process for preparing triarylmethane derivative as defined in claim 1, wherein said triarylmethane derivative having the general formula (I) or (II) is oxidized with use of an oxidizing agent.

9. A process for preparing triarylmethane derivative as defined in claim 8, wherein said oxidizing agent is used in an excess of a stoichiometric amount based on the amount of said triarylmethane derivative having the structural formula (I) or (II).

10. A process for preparing triarylmethane derivative as defined in claim 1, wherein the reaction of said 3-phenylphthalide derivative with said aniline derivative or said indole derivative to form said triarylmethane derivative having the structural formula (I) or (II) is immediately followed by and concurrently occurs with the oxidizing reaction to form said triarylmethane derivative having the structural formula (III) or (IV).

11. A process for preparing triarylmethane derivative as defined in claim 10, wherein said Friedel-Crafts type catalyst comprises at least one member selected from the group of $FeCl_3$, $FeBr_3$, $AgNO_3$, $CuCl_2$ or peracetic acid.

12. A process for preparing triarylmethane derivative as defined in claim 10, wherein said 3-phenylphthalide derivatives having the structural formula (V) has $R_2$ at the 6 position.

13. A process for preparing triarylmethane derivative as defined in claim 12, wherein said $R_2$ is at least one alkyl-, benzyl-, phenyl-, tolyl-, or pentylene-substituted amino group.

14. A process for preparing triarylmethane derivative as defined in claim 11, wherein said Friedel-Crafts type catalyst is used in an excess of the total amount of an equimolar amount with respect to said 3-phenylphthalide derivative and a stoichiometric amount based on the amount of said triarylmethane derivative having the structural formula (I) or (II).

15. A process for preparing triarylmethane derivative as defined in claim 10, wherein the reaction of said 3-phenylphthalide derivative with said aniline derivative or said indole derivative is carried out a temperature within the range of 0° to 180° C.

16. A process for preparing triarylmethane derivatives as defined in claim 1, wherein said triarylmethane derivatives having the structural formula (I) or (II) is oxidized in the presence of at least one oxidizing agent selected from the group consisting of manganese compounds, chromic acid compounds, lead compounds, copper compounds, cobalt compounds, cerium compounds, silver compounds, iron compounds, $SeO_2$, $RuO_4$, $OsO_4$, inorganic peroxides, organic peroxides, halides, oxygen, ozone, ultraviolet rays, sulfoxides, amino acids and chloranil.

17. A process for preparing triarylmethane derivatives as defined in claim 10, wherein the oxidizing agent is selected from the group consisting of ferric chloride, potassium persulfate, chloranil, potassium permanganate, ferric sulfate, sodium hypochlorite, peracetic acid, silver nitrate, lead peroxide, cupric chloride, potassium dichromate and hydrogen peroxide.

18. A process for preparing triarylmethane derivatives as defined in claim 1, wherein said oxidation is with at least one oxidizing agent selected from the group consisting of permanganates, manganese dioxide, manganese (III) salts, chromic anhydride, chromic acid, perchromates, alkyl esters of chromic acid, chromyl chloride, lead compounds, copper compounds, cobalt (III) compounds, cerium (IV) compounds, $NaBiO_3$, bismuthoxide, bismuthacetate, silver (I) compounds, iron (III) compounds, $SeO_2$, $RuO_4$, $OsO_4$, hydrogen peroxide, persulfuric acid, persulfuric acid salts, peroxides of aliphatic or carboxylic acid, hypochlorites, chlorates, hypobromites, bromates, oxygen, ozone, dimethyl sulfoxides, amine oxides and chloranil.

19. A process for preparing triarylmethane derivatives as defined in claim 1, wherein said oxidation is with at least one oxidizing agent selected from the group consisting of permanganates, manganese dioxide, manganese (III) salts, manganese acetate, chromic anhydride, chromic acid, perchromates, chromyl chloride, $PbO$, $PbO_2$, $Pb(OCOCH_3)_4$, $CuO$, $Cu(OH)_2$, $CuSO_4$, $Cu(OCOCH_3)_2$, $CuCl_2$, $CuBr_2$, $Co_2(SO_4)_3$, $Co_3O_4$, $CeO_2$, $Ce(SO_4)_2$, $Ce(SO_4)_3$, $NaBiO_3$, $BiO$, $Bi(OCOCH_3)_2$, $Ag_2O$, $AgOCOCH_3$, $AgNo_3$, $FeCl_3$, $Fe_2(SO_4)_3$, potassium ferricyanate, $SeO_2$, $RuO_4$, $OsO_4$, hydrogen peroxide, persulfuric acid, persulfuric acid salts, performic acid, peracetic acid, perpropionic acid, perbutyric acid, perbenzoic acid, monoperphthalic acid, monoperterephthalic acid, monopersuccinic acid, trifluoroperacetic acid, hypochlorites, chlorates, hypobromites, bromates, oxygen, ozone, sulfoxides, amine oxides and chloranil.

20. A process for preparing a triarylmethane derivative having the structural formula:

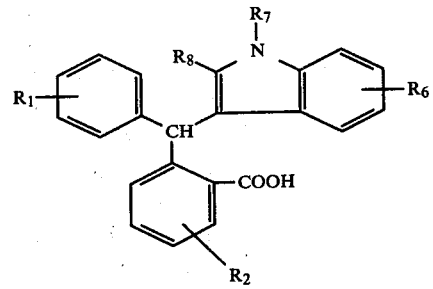

wherein each $R_1$ and $R_2$ represent at least one of hydrogen, halogen, a nitro group, an alkyl group, an amino group, an alkyl-, benzyl-, phenyl-, tolyl-, or pentylene-substituted amino group, a hydroxyl group, an alkyl-substituted hydroxyl group, a thiohydroxyl group or an alkyl-substituted thiohydroxyl group, $R_6$ represents at least one of hydrogen, halogen, lower alkyl group, lower alkoxyl group, amino group, lower alkylamino group, nitro group, phenyl group or phenoxy group, $R_7$ represents hydrogen, alkyl group, aralkyl group or phenyl group, $R_8$ represents an alkyl group or alkyl-, halogen-, or alkoxy-substituted or unsubstituted phenyl group which comprises reacting a 3-phenylphthalide derivative having the structural formula:

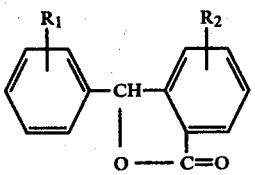

wherein $R_1$ and $R_2$ are the same as described hereinabove, with an indole derivative having the structural formula:

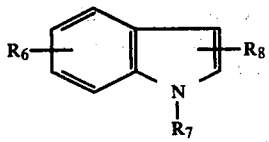

wherein $R_6$, $R_7$ and $R_8$ are the same as hereinabove defined, in the presence of a Friedel-Crafts type catalyst.

21. A process for preparing a triarylmethane derivative having the structural formula:

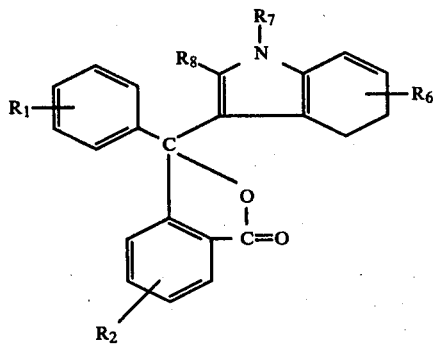

(IV)

wherein each $R_1$ and $R_2$ represents at least one of hydrogen, halogen, nitro group, alkyl group, amino group, alkyl-, benzyl-, phenyl-, tolyl-, or pentylene-substituted amino group, hydroxyl group, alkyl-substituted hydroxyl group, thiohydroxyl group or alkyl-substituted thiohydroxyl group, $R_6$ represents at least one of hydrogen, halogen, lower alkyl group, lower alkoxyl group, amino group, lower alkylamino group, nitro group, phenyl group or phenoxy group, $R_7$ represents hydrogen, alkyl group, benzyl group or phenyl group, $R_8$ represents an alkyl group or alkyl-, halogen-, or alkoxy-substituted or unsubstituted phenyl group which comprises oxidizing a triarylmethane derivative having the structural formula

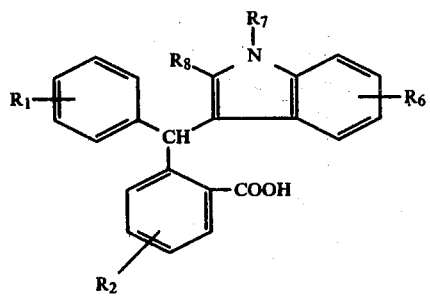

(II)

wherein $R_1$, $R_2$, $R_6$, $R_7$ and $R_8$ are the same as described hereinbefore with an oxidizing agent, said triarylmethane derivative having the structural formula (II) being obtained by the reaction of 3-phenylphthalide having the structural formula

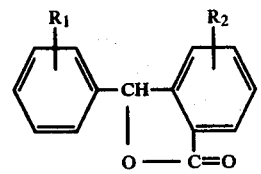

(V)

wherein $R_1$ and $R_2$ are the same as the described hereinbefore with the indole derivative having the structural formula

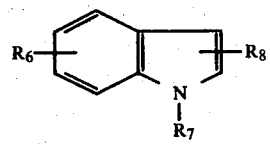

(VII)

wherein $R_6$, $R_7$ and $R_8$ are the same as described hereinbefore in the presence of a Friedel-Crafts type catalyst, said oxidizing agent being at least one selected from the group consisting of permanganates, manganese dioxide, manganese (III) salts, chromic anhydride, chromic acid, perchromates, alkyl esters of chromic acid, chromyl chloride, lead compounds, copper compounds, cobalt (III) compounds, cerium (IV) compounds, $NaBiO_3$, bismuthoxide, bismuthacetate, silver (I) compounds, iron (III) compounds, $SeO_2$, $RuO_4$, $OsO_4$, hydrogen peroxide, persulfuric acid, persulfuric acid salts, peroxides of aliphatic or carboxylic acid, hypochlorites, chlorates, hypobromites, bromates, oxygen, ozone, dimethyl sulfoxides, amine oxides and chloranil.

22. A process for preparing a triarylmethane derivative as claimed in claim 18 wherein each $R_3$ and $R_4$ represents hydrogen, an alkyl group, a benzyl group, or a phenyl group.

23. A process for preparing a triarylmethane derivative having the structural formula

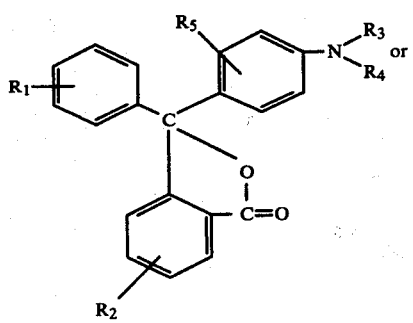

(III)

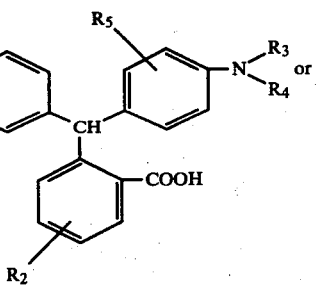

(I)

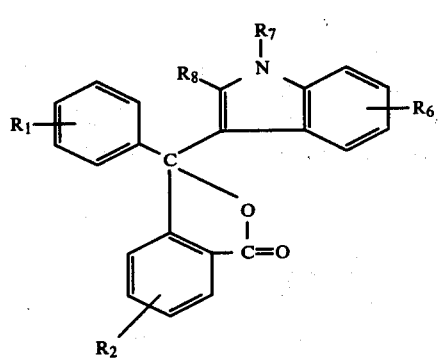

(IV)

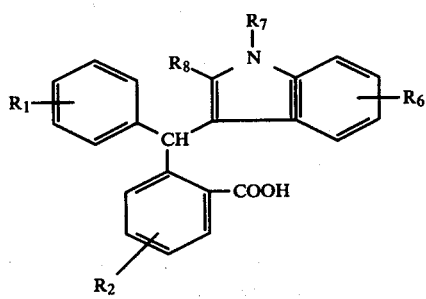

(II)

wherein each $R_1$ and $R_2$ represents at least one of hydrogen, halogen, nitro group, alkyl group, amino group, alkyl-, benzyl-, phenyl-, tolyl-, or pentylene-substituted amino group, hydroxyl group, alkyl-substituted hydroxyl group, thiohydroxyl group or alkyl-substituted thio-hydroxyl group, each $R_3$ and $R_4$ represents hydrogen, cyano-, hydroxyl-, halogen-, methoxy-, ethyoxy-, or ethoxycarbonyl-substituted or unsubstituted alkyl group, cycloalkyl group, alkyl-substituted or unsubstituted aralkyl group, aryl group, or unsaturated alkyl group, or one or both of $R_3$ and $R_4$ together with the adjacent nitrogen atom may form a morpholine ring, a pyrrolidine ring, a pyrazolidine ring, a piperidine ring, an imidazoline ring, a piperazine ring, or a pyrimidine ring, $R_5$ represents at least one of hydrogen, halogen, alkyl group, nitro group, lower alkyl-substituted or unsubstituted amino group, lower alkyl-substituted or unsubstituted hydroxyl group, or lower alkyl-substituted or unsubstituted thiohydroxyl group, $R_6$ represents at least one of hydrogen, halogen, lower alkyl group, lower alkoxyl group, amino group, lower alkylamino group, nitro group, phenyl group or phenoxy group, $R_7$ represents hydrogen, alkyl group, aralkyl group or phenyl group, $R_8$ represents an alkyl group or alkyl-, halogen-, or alkoxy-substituted or unsubstituted phenyl group which comprises oxidizing a triarylmethane derivative having the structural formula wherein $R_1$, $R_2$, $R_3$, $R_4$, $R_5$, $R_6$, $R_7$ and $R_8$ are the same as described hereinbefore, said triarylmethane derivative having the structural formula (I) or (II) being obtained by the reaction of 3-phenylphthalide having the structural formula

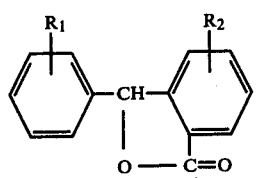

(V)

wherein $R_1$ and $R_2$ are the same as described hereinbefore with the aniline derivative having the structural formula

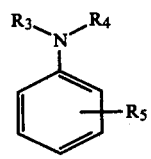

(VI)

wherein $R_3$, $R_4$ and $R_5$ are the same as described hereinbefore, or with the indole derivative having the structural formula

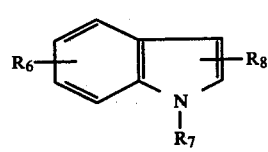

(VII)

wherein $R_6$, $R_7$ and $R_8$ are the same as described hereinbefore in the presence of a Friedel-Crafts type catalyst.

* * * * *